US008854629B2

(12) United States Patent
Frisken et al.

(10) Patent No.: US 8,854,629 B2
(45) Date of Patent: Oct. 7, 2014

(54) OPTICAL COHERENCE TOMOGRAPHY SYSTEM AND METHOD

(75) Inventors: Steven James Frisken, Vaucluse (AU); Daniel Royston Neill, St. Marys (AU)

(73) Assignee: Finisar Corporation, Horsham, PA (US)

( * ) Notice: Subject to any disclaimer, the term of this patent is extended or adjusted under 35 U.S.C. 154(b) by 175 days.

(21) Appl. No.: 13/297,356

(22) Filed: Nov. 16, 2011

(65) Prior Publication Data

US 2012/0120407 A1    May 17, 2012

Related U.S. Application Data

(60) Provisional application No. 61/414,727, filed on Nov. 17, 2010.

(51) Int. Cl.
*G01B 9/02*    (2006.01)
*G01N 21/47*    (2006.01)

(52) U.S. Cl.
CPC ........ *G01B 9/02069* (2013.01); *G01B 2290/45* (2013.01); *G01B 9/02081* (2013.01); *G01N 21/4795* (2013.01); *G01B 2290/70* (2013.01); *G01B 9/02004* (2013.01); *G01B 9/02091* (2013.01)
USPC .......................................... 356/491; 359/479

(58) Field of Classification Search
USPC ................... 356/479, 491, 495, 497
See application file for complete search history.

(56) References Cited

U.S. PATENT DOCUMENTS

| 6,327,019 | B1 | 12/2001 | Patel et al. | |
|---|---|---|---|---|
| 7,019,838 | B2 | 3/2006 | Izatt et al. | |
| 8,526,830 | B2* | 9/2013 | Frisken | 398/202 |
| 2002/0131691 | A1 | 9/2002 | Garrett et al. | |
| 2007/0035743 | A1* | 2/2007 | Vakoc et al. | 356/495 |
| 2007/0285669 | A1* | 12/2007 | Ajgaonkar et al. | 356/482 |
| 2010/0074632 | A1* | 3/2010 | Zhou | 398/208 |

FOREIGN PATENT DOCUMENTS

| WO | 03/032071 A1 | 4/2003 |
|---|---|---|
| WO | 2004/005993 A1 | 1/2004 |

OTHER PUBLICATIONS

Vakhtin, et al., Demonstration of Complex-Conjugate-Resolved Harmonic Fourier-Domain Optical Coherence Tomography Imaging of Biological Samples, Applied Optics, Jun. 20, 2007, pp. 3870-3877, vol. 46, No. 18, Optical Society of America, USA.
"Supplementary Search Report" for EP 05749258.9-2217/1766819, Jan. 21, 2013, European Patent Office, Munich, Germany.

* cited by examiner

*Primary Examiner* — Michael A Lyons
(74) *Attorney, Agent, or Firm* — Kurt Rauschenbach; Rauschenbach Patent Law Group, LLC

(57) ABSTRACT

A method of analysis of a sample, including the steps of: (a) splitting an input optical beam into a probe beam and reference beam; (b) utilizing the probe beam to interrogate a sample and obtaining a return sample beam there from; (c) manipulating the reference beam into a predetermined polarization state; (d) mixing the return sample beam and reference beam producing a series of mixed beams; and (e) analyzing the polarization components of the series of mixed beams.

20 Claims, 20 Drawing Sheets

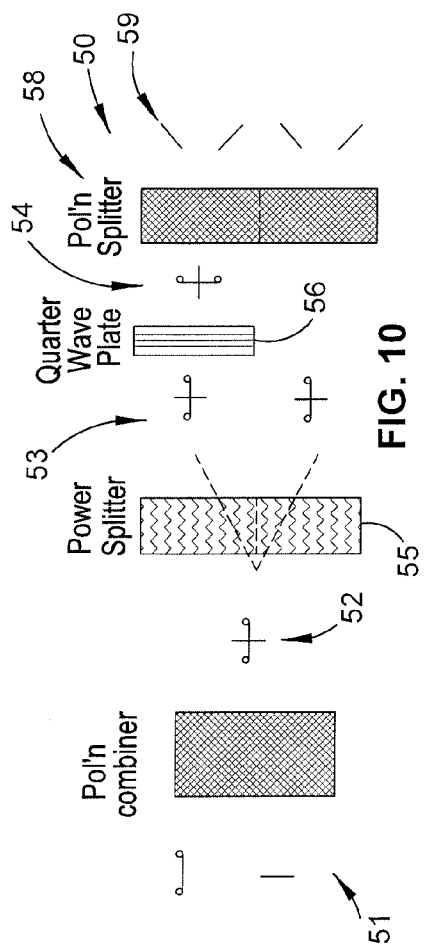
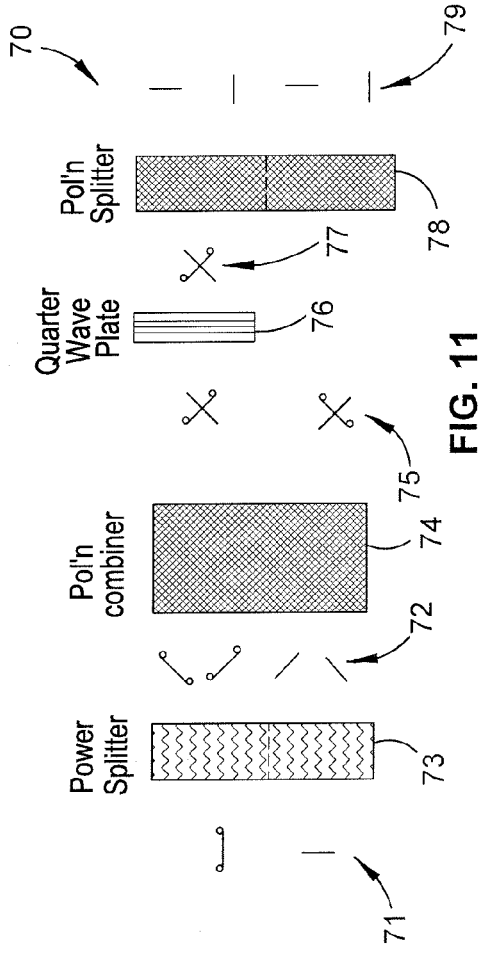
FIG. 10
FIG. 11

OPTICAL COHERENCE TOMOGRAPHY SYSTEM AND METHOD

CROSS-REFERENCE TO RELATED APPLICATIONS

The present application is a non-provisional of copending U.S. Provisional Patent Application Ser. No. 61/414,727, filed on Nov. 17, 2010. The entire contents U.S. Patent Application Ser. No. 61/414,727 is herein incorporated by reference.

FIELD OF THE INVENTION

The present invention relates to the detection of signals in an optical coherence tomography system. In particular, the invention provides for the simultaneous detection of both polarization and phase resolved signals. The invention includes an optical imaging engine whose modular design allows for simple integration into diverse OCT systems.

DESCRIPTION OF THE BACKGROUND ART

Optical Coherence Tomography (OCT) is an imaging technique that allows micrometer scale imaging over short distances. It is based on a novel extension of optical coherence domain reflectometry (OCDR), a one dimensional optical ranging technique used for investigating the properties of fiber and waveguide based optical devices. OCT relies on the coherent interference between a reference wave and a probe wave to measure the distances and thicknesses of a material. Extensions exist to measure flow, refractive indexes, and the polarization properties of samples under test.

Due to its non-contact, non-invasive and non-destructive nature, OCT has found extensive application in the biomedical imaging field, ranging from ophthalmology to neurology, dermatology, dentistry, developmental biology, urology, and gastroenterology as an in-vivo diagnostic tool. The properties of OCT imaging also have applications many non-biomedical applications ranging from dimensional metrology, material research and non-destructive testing, over art diagnostics, botany, microfluidics, to data storage and security applications. Currently developing OCT techniques have high potential for future applications both inside and outside the scope of the biomedical field.

Generally, optical coherence tomography systems can be divided into three main types depending on how the depth information is obtained. If the depth ranging is obtained by varying the path length difference between the sampling and reference arms in time, the configuration is referred to as time-domain optical coherence tomography (TD-OCT). TD-OCT systems are usually implemented with a movable mirror in the reference arm of the interferometer to provide the path length difference. When depth information is extracted from the spatial variation of the interferometric signals spectral components the system is known as spectral domain optical coherence tomography (SD-OCT). The temporal variation of the spectral components is known as swept source optical coherence tomography (SS-OCT). Due to the spectral nature of both SS-OCT and SD-OCT, they are both also known under the title of Fourier domain optical coherence tomography (FD-OCT).

Examples of the architectures are shown schematically in FIG. 1 to FIG. 4. The FD-OCT architectures offer increased speed and theoretical sensitivity when compared to TD-OCT systems. FIG. 1 is a schematic block diagram of a basic optical coherence tomography system to which the proposed system is applicable. FIG. 2 is a schematic block diagram of a time domain optical coherence tomography system as described in the prior art. FIG. 3 is a schematic block diagram of a spectral domain optical coherence tomography system as described in the prior art. FIG. 4 is a schematic block diagram of a swept source optical coherence tomography system as described in the prior art In the above prior art arrangements, it is advantageous to fully decode the output signal in order to have both the phase and amplitude information of the received signal. In Doppler OCT, multiple measurements of the phase can be used to increase the velocity sensitivity. In FD-OCT systems the lack of phase information leads to a known complex conjugate ambiguity, where the positive and negative spatial frequencies of the signal cannot be separated. This complex conjugate ambiguity results in image contamination with double images, undesirable autocorrelation terms and wasted resources (pixels in SD-OCT and time in SS-OCT) due to a reduction in imaging depth. See, for example, "Demonstration of complex-conjugate-resolved harmonic Fourier-domain optical coherence tomography imaging of biological samples", Vakhtin et al., Applied Optics, Vol 46, No. 18, p 3670.

As the opto-electronic conversion process relies on square law detectors, the phase information in the interferometric signal is lost upon detection and only the real part of the signal is obtained. This results in a complex conjugate ambiguity that cannot be resolved or removed via post processing, necessitating the use of the full complex signal to remove the ambiguity.

Various methods reported that allow for the recovery of the full complex signal include the use of polarization quadrature encoding, phase stepping, N×N couplers (with N≥3) and synchronous detection. In polarization quadrature encoding, orthogonal polarization states encode the real and imaginary parts of the signal, but the setup is complex and the signal suffers from polarization fading as the reference and sample arms approach a quasi-orthogonal state. Phase stepping requires the reference mirror to be sequentially displaced encoding the real and imaginary components in time. However, phase stepping is not instantaneous and sensitive to small drifts in the interferometer. Synchronous detection requires the signal is mixed in a heterodyne arrangement where the complex signal is generated electronically (as opposed to the previously mention methods where the signal is generated optically). Relying on an electronic carrier frequency, synchronous detection is unsuitable for homodyne detection systems, such as in FD-OCT setups. The use of couplers (N×N with N≥3) couplers generate signals with a non 180° phase shift from which the complete complex signal can be calculated by the cosine rule.

Polarization fading is also a problem for most interferometric systems. The main methods to avoid its effects are either to recover the full polarization information or through strict control of the polarization states as the light beams pass through the interferometer. This often requires the use of polarization beam splitters, polarization maintaining fibers or a doubling of the receiver structure (one for each polarization).

SUMMARY OF THE INVENTION

It is an object of the present invention to provide an improved form of OCT decoder.

In accordance with a first aspect of the present invention, there is provided a method of analysis of a sample, including the steps of: (a) splitting an input optical beam into a probe beam and reference beam; (b) utilizing the probe beam to interrogate a sample and obtaining a return sample beam there from; (c) manipulating the reference beam into a predetermined polarization state; (d) mixing the return sample beam and reference beam producing a series of mixed beams; and (e) analyzing the polarization components of the series of mixed beams.

The mixing step further preferably can include the steps of: dividing the reference beam into substantially polarization orthogonal reference components; dividing the return sample beam into substantially polarization orthogonal return sample components; and mixing the reference components with the sample components to produce a series of mixed beams.

The mixing preferably can include obtaining sum and difference components of the mixed reference components. The substantially polarization orthogonal reference components can comprise horizontal and vertical components. The analyzing step preferably can include outputting the quadrature signal components of the combination of the probe and reference beam.

The splitting step further can comprise splitting the input optical beam into a triggering beam and the analyzing step further can comprise utilizing the triggering beam to initiate sampling of the polarization components.

In accordance with a second aspect of the present invention, there is provided an optical signal analysis system comprising: an optical source; a beam splitter interconnected to the optical source for splitting the source into a probe beam and reference beam; a sampling unit for utilizing the probe beam to interrogate a sample and obtain a return probe beam therefrom; A length matching unit for correlating the reference beam length with the return probe beam length; a polarization manipulation unit for manipulating the polarization state of the correlated reference beam into a predetermined polarization state; and a polarization analysis unit for mixing substantially orthogonal polarization components of the correlated reference beam with the return probe beam.

In accordance with a third aspect of the present invention, there is provided a receiver for an OCT system, the receiver comprising: a first input port for receiving an OCT probe beam reflected from a sample; a second input port for receiving an OCT reference beam transmitted along an optical path substantially matched to the probe beam optical path; a polarization manipulation unit for: dividing the reference beam into substantially polarization orthogonal reference components; and dividing the probe beam into substantially polarization orthogonal probe components; and an analysis unit for mixing reference and probe components to produce a series of mixed beams.

The analysis unit is preferably a fiber coupled coherent receiver. The analysis unit preferably includes:
 a first mixer for mixing a first orthogonal reference component with a first orthogonal probe polarisation component to provide a first mixed signal;
 a second mixer for mixing a second orthogonal reference component with a second orthogonal probe polarisation component to provide a second mixed signal;
 an analyser for analysing the first and second mixed signals to determine the polarisation or phase information in the OCT probe beam.

The analyser preferably includes:
 a splitter for splitting the power of the first mixed signal into at least a first and second mixed sub-signals;
 a delay element for delaying one orthogonal polarisation component of the first sub-signal relative to the second component by pi/2 radians to produce a phase delayed first sub-signal;
 a dividing unit for dividing the phase delayed first sub signal into orthogonal components and the second mixed sub-signal into orthogonal components.

The receiver of the third aspect preferably outputs the following four quadrature phase mixed beams in a first x polarization state:

$$E_x^s + E_x^R, E_x^s - E_x^R, E_x^s + iE_x^R, E_x^s + iE_x^R;$$

and the following four quadrature phase mixed beams in a second in a second y polarization state:

$$E_y^s + E_y^R, E_y^s - E_y^R, E_y^s + iE_y^R, E_y^s + iE_y^R;$$

where E represents an electric field strength, R indicates a reference signal component and S indicates a probe signal component.

The receiver of the third aspect preferably includes four balanced photodetectors, each configured for simultaneously receiving a corresponding quadrature phase beam of each polarization state.

BRIEF DESCRIPTION OF THE DRAWINGS

The invention will be described in detail with reference to the accompanying drawings, with reference characters referring to like elements with emphasis being placed upon illustrating the principles of the invention. Of the drawings:

FIG. 10 illustrates one for of component implementation of the arrangement of FIG. 9;

FIG. 11 illustrates a second form of component implementation of the arrangement of FIG. 9;

DETAILED DESCRIPTION OF THE PREFERRED AND OTHER EMBODIMENTS

In the preferred embodiments there is provided an optical engine that can deliver both phase and polarization information with reduced processing overhead in a compact form with minimal components. Being robust and possessing a flexible architecture provides an arrangement that is easily integrated into many current systems. The preferred embodiments also limit the offline processing needed for the system allowing for real time OCT imaging devices.

Figure 1:
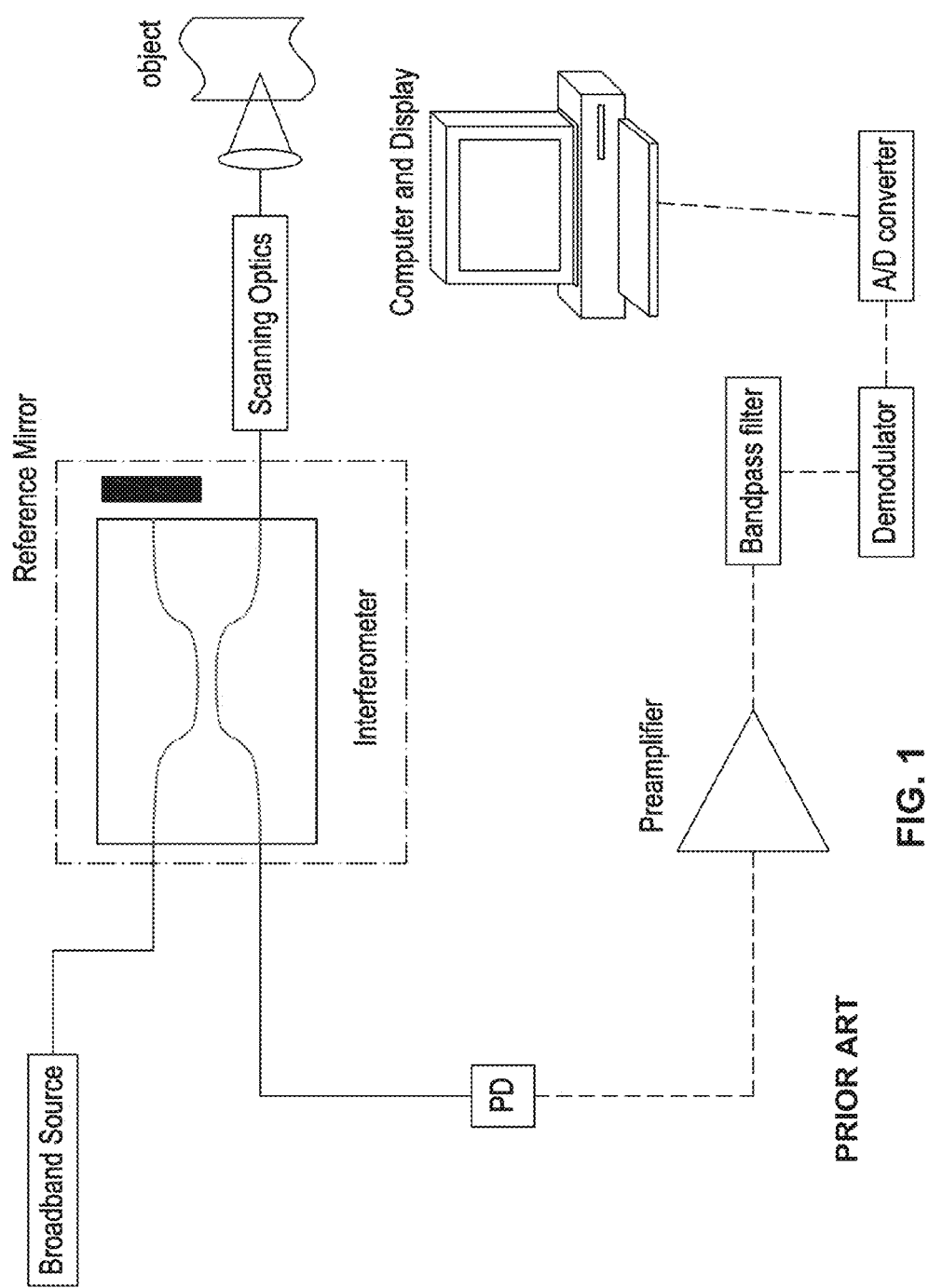
FIG. 1 is a schematic block diagram of a basic optical coherence tomography system to which the proposed system is applicable.
Figure 2:
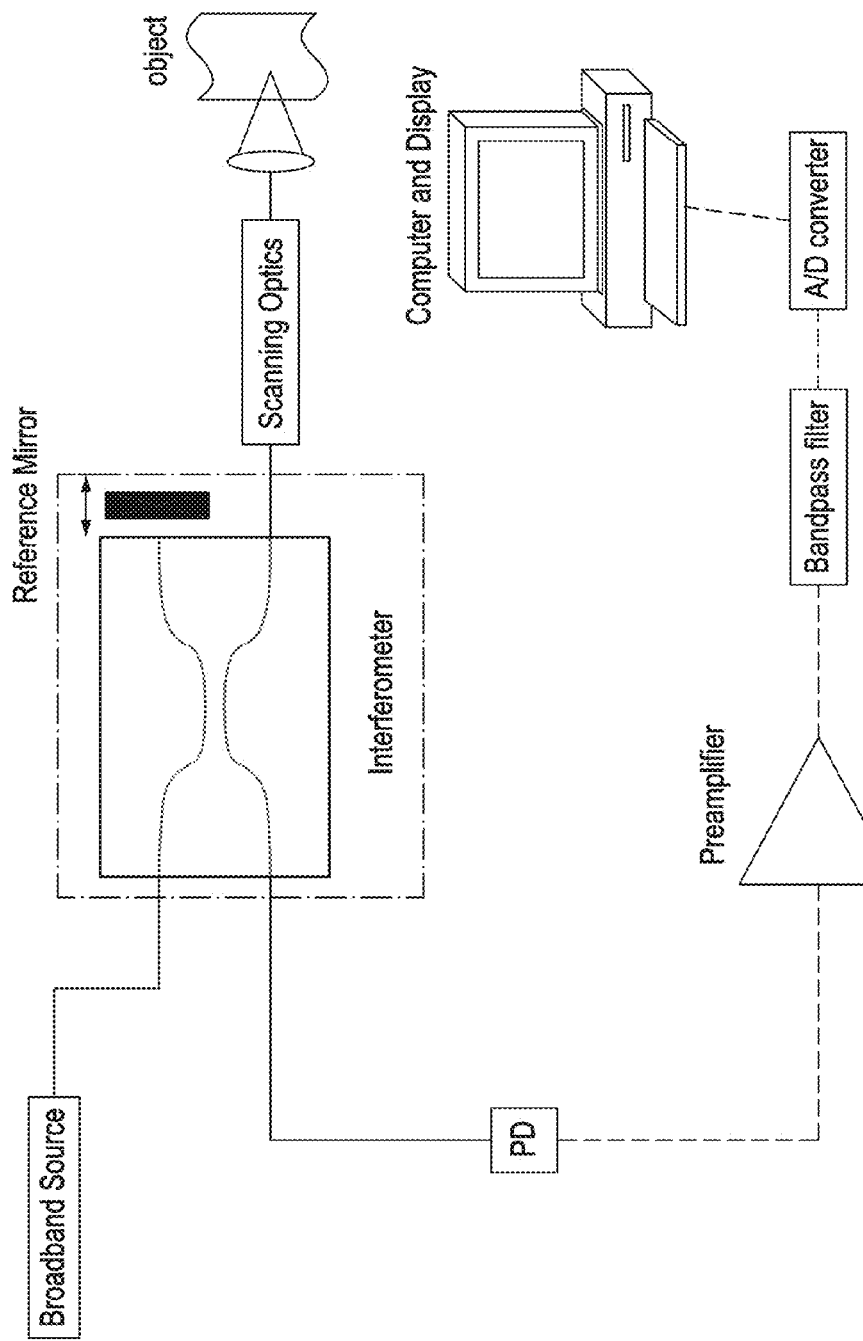
FIG. 2 is a schematic block diagram of a time domain optical coherence tomography system as described in the prior art.
Figure 3:
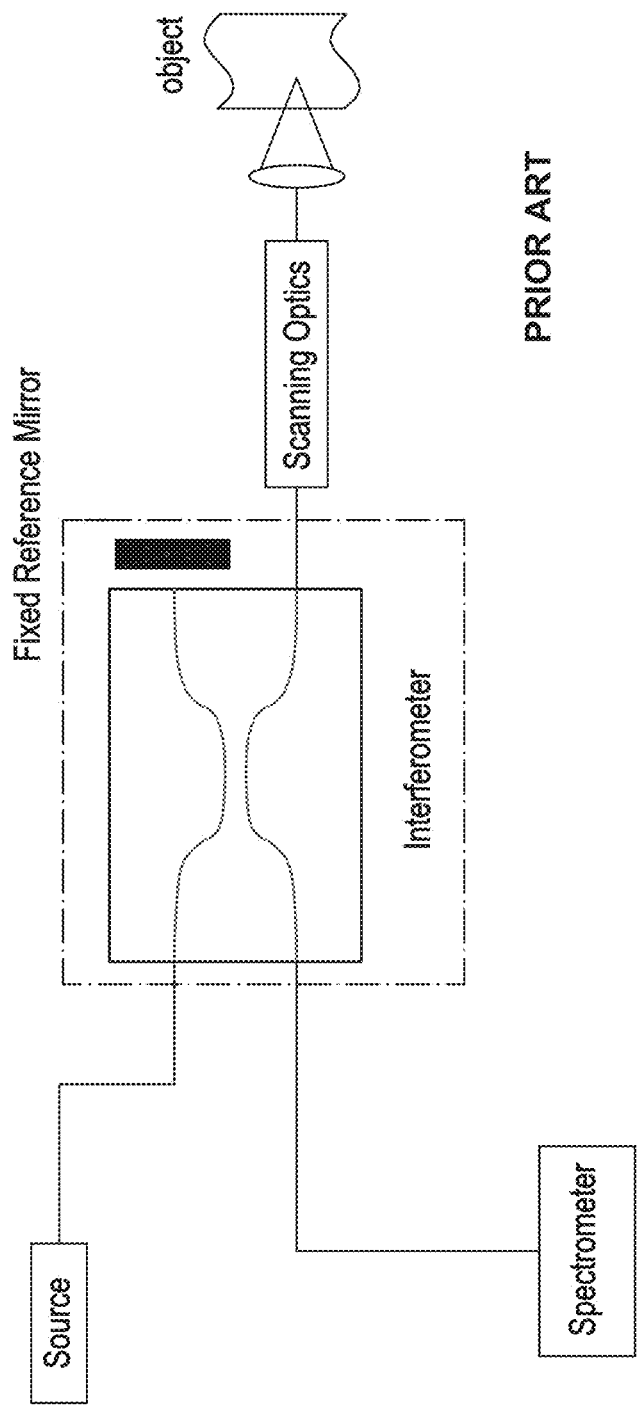
FIG. 3 is a schematic block diagram of a spectral domain optical coherence tomography system as described in the prior art.
Figure 4:
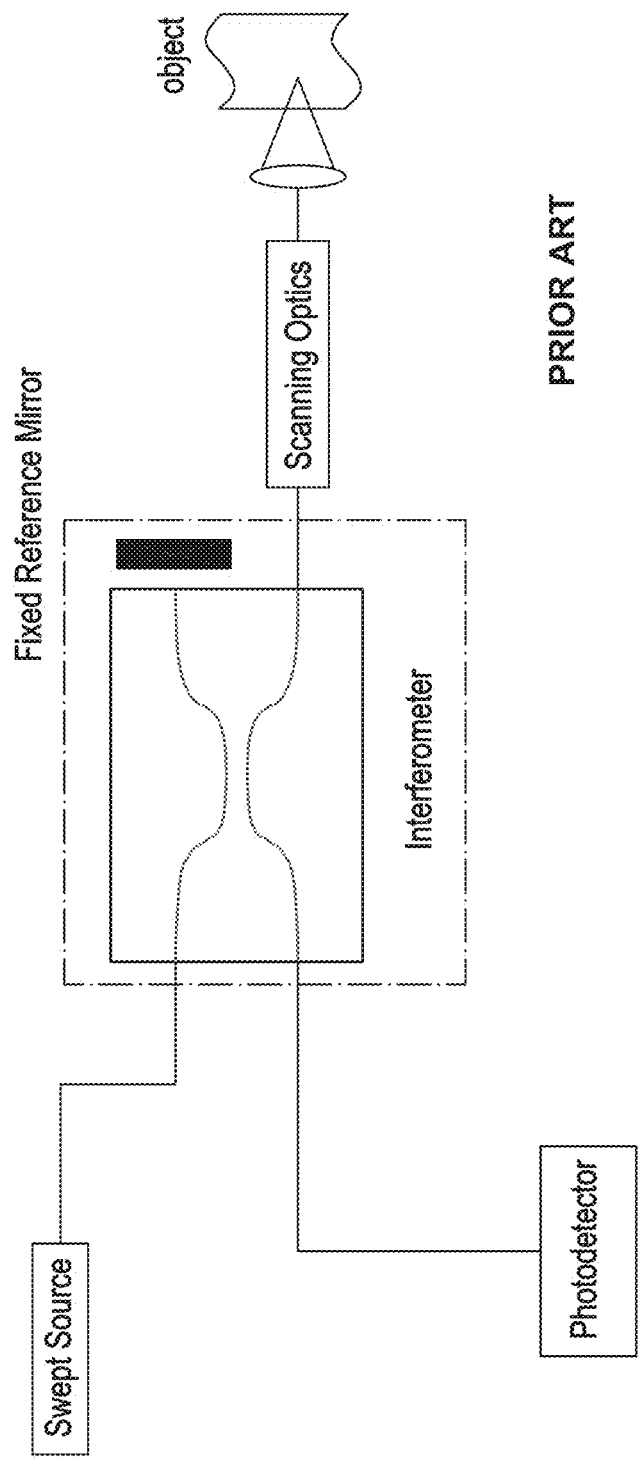
FIG. 4 is a schematic block diagram of a swept source optical coherence tomography system as described in the prior art.
Figure 5:
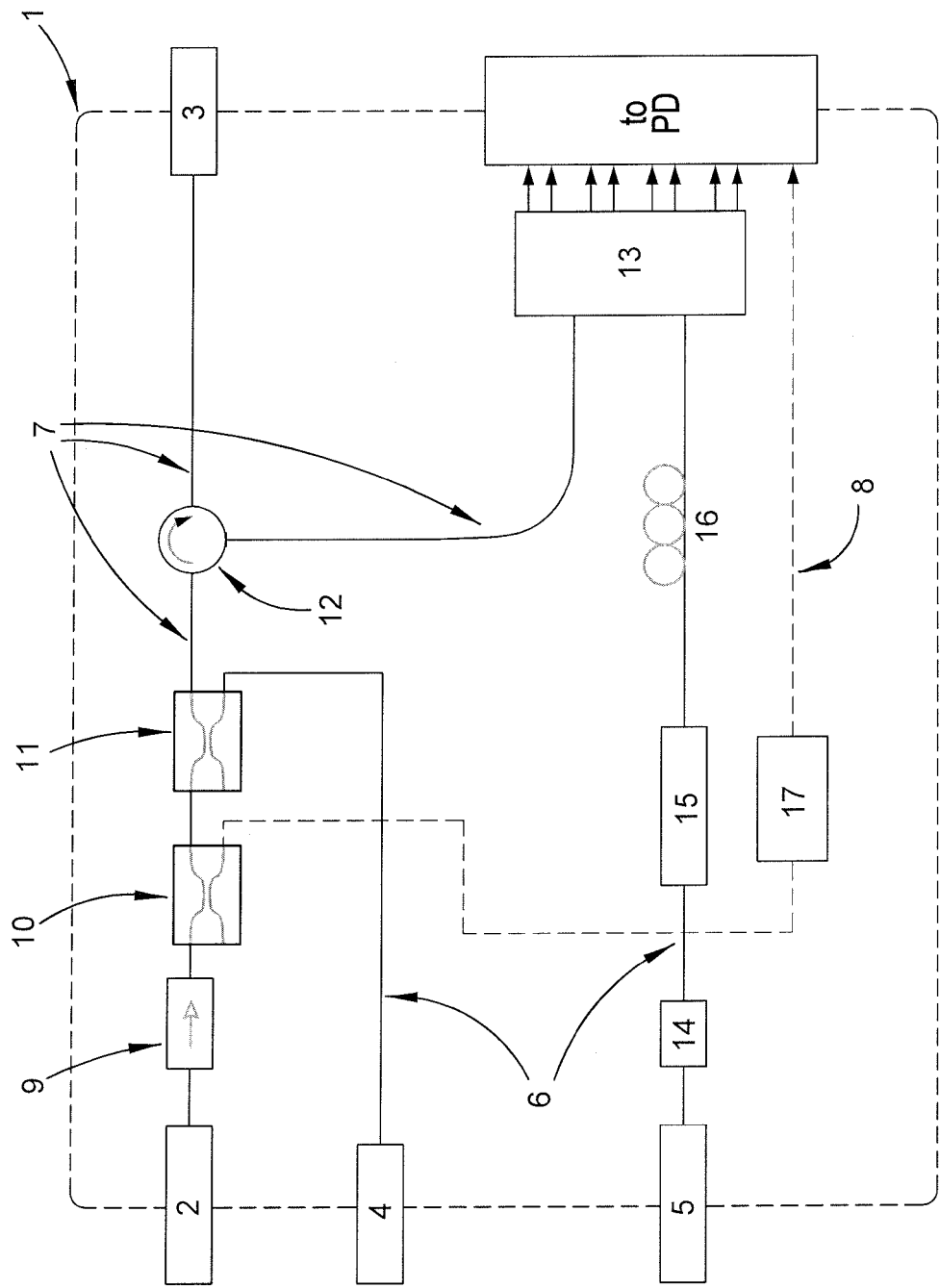
FIG. 5 is a schematic block diagram of the optical components of an embodiment of the present invention.

FIG. 5 shows the preferred embodiment of an optical engine 1 constructed in accordance with the principles of the present invention. The optical engine includes four inputs (2-5) that enable the OCT optical engine to be integrated into different OCT architectures. Port 2 connects the light source into the device such as swept source lasers (used in SS-OCT) and broadband light sources (used in FD-OCT and TD-OCT). Port 3 connects the OCT probe to the device and allows for different probes to be integrated into the device to perform a wide variety of tasks. Ports 4 and 5 are used to form the reference arm 6 when appropriately connected and allow for further architecture variation. The sample arm of the OCT system is provided 7 while path 9 (shown in FIG. 5 as a dotted path) is included for triggering purposes.

Light entering the device through input port 2 initially passes through an isolator 9 which prevents back reflections. It then passes through a splitter 10 where some of the incident power is tapped to the triggering circuit 8. In the preferred embodiment this amount of power small, such as in a 99/1 splitting ratio, in order to maximize the incident power upon the sample. The majority of the incident light continues to another splitter 11 which splits the light between the reference arm 6 and sample arm 6 of the interferometer. The coupling ratio of the splitter 11 is preferred such that the majority of the incoming light from input 2 enters the sample arm 7. The light in 6 then travels through a 3 port optical circulator 12 and then passes on to the probe input/output port 3. The port 3 is attached to an output probe for interrogating a sample and obtaining a back reflection therefrom.

Light backscattered from the sample under test is reflected back along the probe into the probe input/output port 3 to the circulator 12, which then routes the light to a coherent polarization analyzer (CPA) 13. In one embodiment, CPA 13 can be realized as a 2×8 fiber coupled polarization diverse coherent optical receiver module, which is capable of extracting both phase and polarization information from a signal. In another embodiment, CPA 13 includes one or more coherent optical receivers in addition to other components and some of the functionality of CPA 13 is performed by the one or more coherent optical receivers.

Light from the coupler 11 also enters the reference arm 6 and travels to port 4. The reference arm 6 is completed by providing a path for light to travel between 4 and 5 such that the length of the reference arm 6 is similar to that of the sample arm 7. The return light entering at port 5 then passes through a variable optical attenuator (VOA) 14, a tunable delay line 15 and a polarization controller 16 into a CPA module 13. The VOA 14 is used to control the signal power level incident upon the CPA 13 from the reference arm 6 while the tunable delay line 15 is used to closely match the path lengths between the sample 7 and reference arm 6. Following the tunable delay line 15, the polarization controller 16 is to put the polarization in the correct state for the mixing (45° for a linearly polarized source) as the CPA 13 is sensitive to the polarization state in the reference arm 6. An optical dispersion compensator can also be added into the reference arm to compensate for dispersion in the sample arm (consisting of the fibre path and the samples optical properties). Other dispersion compensation methods can be easily incorporated, either through signal processing on the electronic signal or appropriate triggering in the k-space.

The optical paths inside the OCT engine 1 can be constructed using free space optics or optical fibers, optical fibers being the preferred form. The fibers can be either standard single mode (SM) or polarization maintaining (PM) fibers. As for the sample arm 7, either SM or PM fiber (or any combination) can be used in the reference arm 6.

The preferred embodiment of the optical engine 1 consists of SM fiber used throughout the device, except for between the polarization controller 16 and the CPA 13 where PM fiber is used. In this instance the fiber birefringence can be compensated in the electronic domain, methods including the use of a constant polarization reference signal and calibration scans.

The triggering arm 8 is used to generate a triggering signal that is linear in the wave-space to compensate for any non-linearity in the wavelength sweep of the source. The triggering signal can be used to monitor the output characteristics of the source. This triggering or monitoring can be accomplished by sampling the input signal with a coupler 10 and passing the signal through an interferometer 17. When used for trigger sampling, the FSR of the interferometer 17 determines the linear frequency spacing between samples. Implementations of the interferometer 17 include a Mach Zehnder interferometer (MZI) or a Fabry Perot interferometer (FPI). Both MZI and FPI can be constructed out of either fiber or bulk optic components. In one embodiment, the beams output from the system can be selectively modified, prior to detection, based upon the monitoring of the input optical beam from the source.

Figure 8:
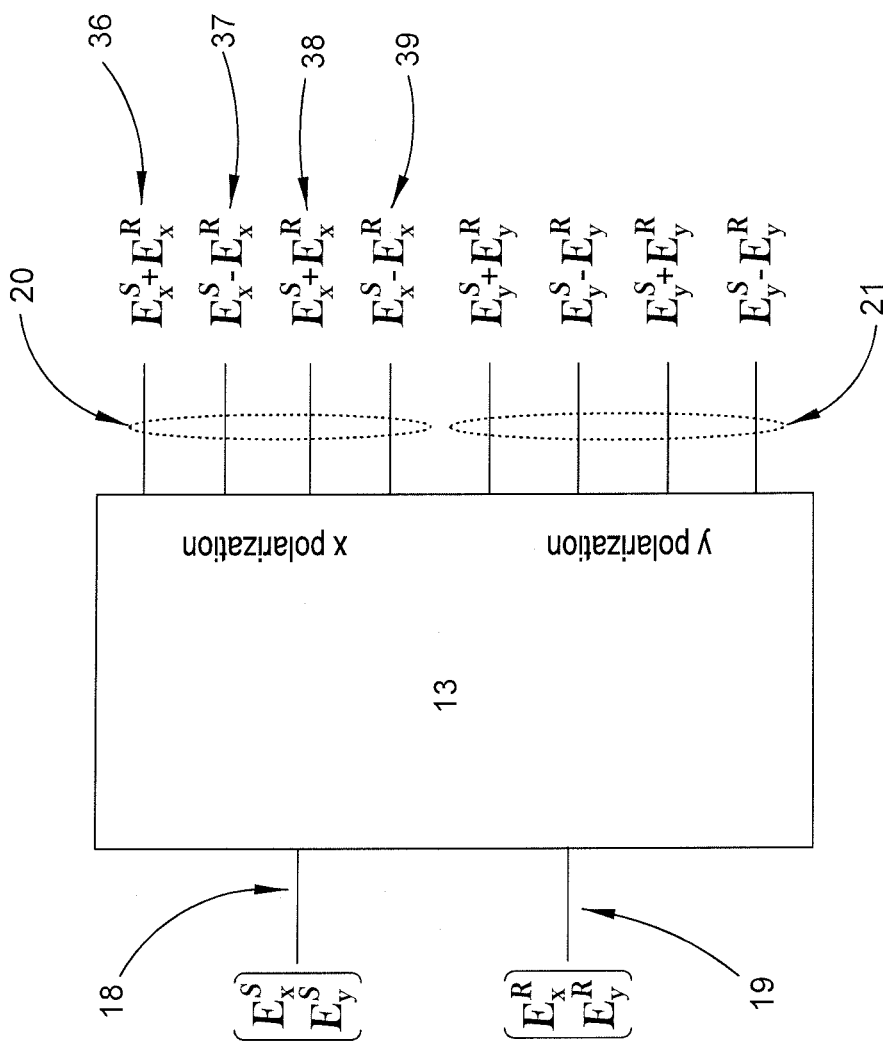
FIG. 8 is a block diagram illustrating the relation of the inputs to the outputs of the Coherent Polarization Analyzer (CPA) component of the present invention.

A block diagram of a Coherent Polarization Analyzer (CPA) 13 is initially shown in FIG. 8. In this figure the polarization states are written in terms of Jones vectors. While the relations are shown for linear polarizations, similar relations hold for other orthogonal polarization states. The CPA 13 requires two input optical signals (18 and 19) and produces eight output optical signals (20 and 21). The inputs 18 and 19 are connected to the output of the sample arm 7 and the output of the reference arm 6 respectively.

The input signals 18, 19 can be represented by Jones Vectors $$\begin{bmatrix} E_x^S \\ E_y^S \end{bmatrix}, \begin{bmatrix} E_x^R \\ E_y^R \end{bmatrix}$$

respectively. The two input signals 18 and 19 are mixed to produce eight outputs, four for each polarization state, resulting in the following outputs: $E_x^R$, $E_x^s - E_x^R$, $E_x^s + iE_x^R$, $E_x^s + iE_x^R$; $E_y^s + E_y^R$, $E_y^s - E_y^R$, $E_y^s + iE_y^R$, $E_y^s + iE_y^R$. Each set of four mixed signals (corresponding to 20 and 21) consists of mixing with 0°, 90°, 180° and 270° phase shifts between the input signals 18 and 19.

Figure 9:
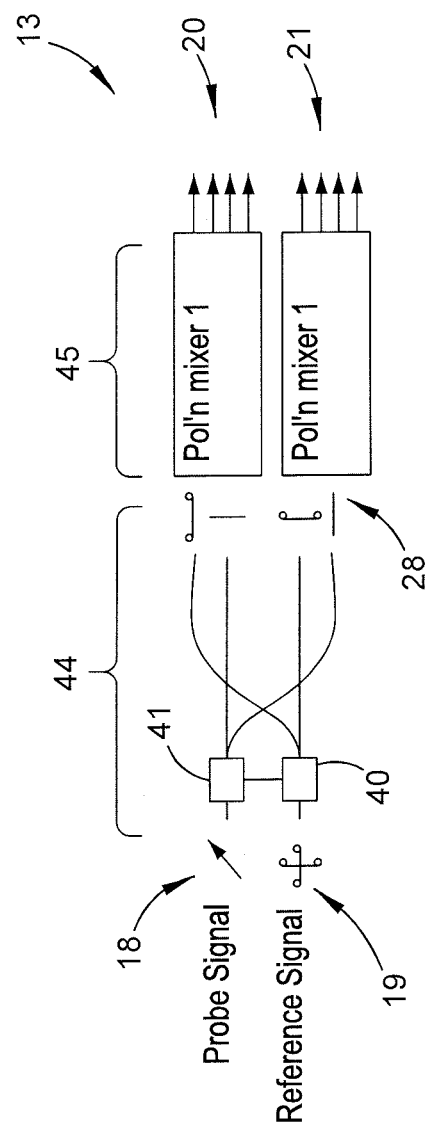
FIG. 9 illustrates schematically one form of CPA.

Turning to FIG. 9, there is illustrated schematically the general structure of a first embodiment CPA 13. In this unit 13, the inputs include the reference signal input 19 having a 45 degree polarization state, in addition to the probe input signal 18. The signal 18 is made up of orthogonal polarizations within each of the orthogonal polarization components.

The first embodiment comprises two primary stages. The first stage 44 separates orthogonal components of the input reference signal 19 and the probe signal 18. This is achieved by utilizing a polarization splitting crystal 40, 41. Each of the polarization splitters split the polarization into vertical and horizontal components. The next stage 45 analyses each of the orthogonal polarizations by means of a polarization mixer. The polarization mixer outputs 20, 21 can either be fiber coupled to outputs or coupled to a PIN-TIA array of detectors at a small pitch.

In the arrangement 13, the polarization states upon input to the mixer stage 45 are orthogonal. The polarization mixer relies on combining orthogonal polarization states of signal and local oscillator and then analyzing the generated polarization state to generate the required signals.

Turning now to FIG. 10, there is illustrated an example of the operation of each of the polarization mixers 45 of FIG. 9. The first polarization stage takes orthogonal polarization inputs 51 and combines them 52. Then they are split 53 with the power split into upper and lower channels. In one embodiment, the splitter could be a transmission grating with periodic structure designed to provide an angular separation between positive and negative orders of the grating or could be provided by a partial mirror.

One of those channels undergoes a polarization retardation 54 by means of quarter wave plate 56. Next polarization splitter 58 splits the polarization states into diagonal orthogonal components to provide outputs 59.

An alternative arrangement of the polarization mixer is illustrated 70 in FIG. 11. In this arrangement, the power splitting process is moved before the polarization combination. The input polarizations 71 are subject to a power splitting 72 via power splitter 73. Next polarization combiner 74 combines the split power combinations to produce output 75. One of the combinations is then subject to rotation via quarter wave plate 76 so as to produce output 77. Next, polarization splitter 78 separates orthogonal polarizations to produce separated outputs 79.

Figure 12:
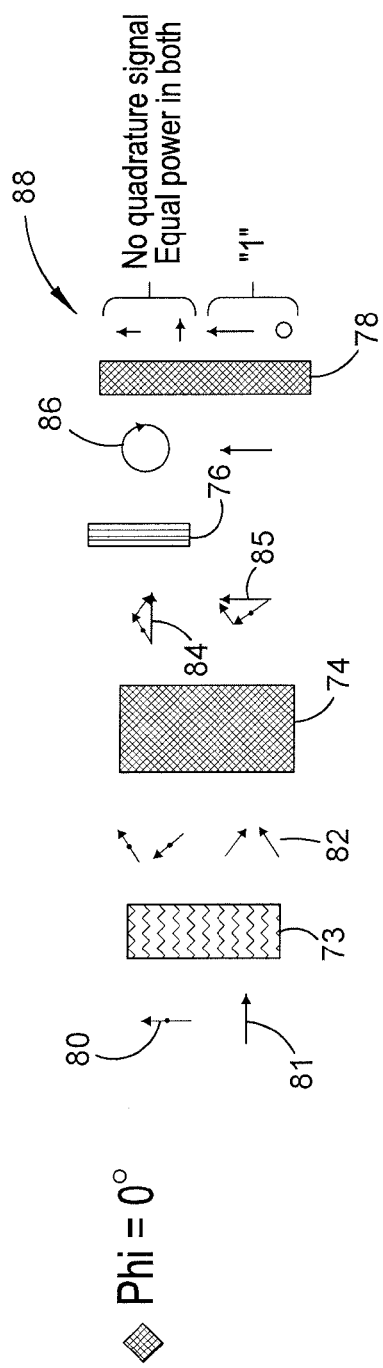
FIG. 12 and FIG. 13 illustrate polarization evolution for light travelling through the arrangement of FIG. 9.
Figure 13:
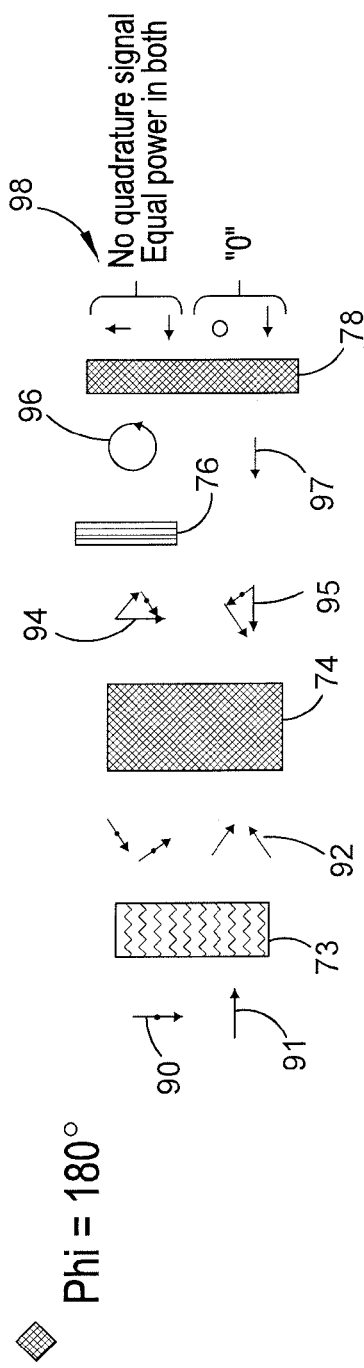

A simple example explanation of operation of the mixer will now be described. For simplicity of explanation, FIG. 12 and FIG. 13 illustrate examples of polarization state transformation in the polarization mixer. Taking initially FIG. 12, the case of decoding the Phi=0 degrees phase signal is illustrated. The input polarization 80 vertical component is processed as follows. The reference mixer input 81 is in the horizontal state. The power splitter 73 splits the power of the input producing polarization outputs 82. The combiner 74 combines the two polarization states into their vector sum. In this case the two inputs are combined 'vectorially' to produce vector sums 84, 85. The quarter wave plate 76 delays one polarization axis relative to the other so that horizontal polarization state 84 is transformed into circular polarization state 86. The polarization splitter 78 then provides polarization outputs 88. In this particular instance of Phi=0, where no quadrature signal is encoded and only binary phase demodulation is implemented, equal power is initially distributed into each top channel so that no distinguishable quadrature signal is output. However, in the bottom two channels, the equivalent of a binary '1' is output with all the power from the vertical polarization state 85 going into one channel and zero power being output into the other channels.

FIG. 13 illustrates the case when Phi=180 degrees and it can be seen that similar processing occurs through the element 73, 74, 76 and 78. Initially, the polarization states 90, 91 are distributed 92 by element 73. Next, they are combined vectorially via polarization combiner 74 to produce vectorially combined polarization states 94, 95. The polarization state 94 is subject to quarter wave plate relative delay to produce elliptical/circular polarization state 96 with the polarization state 95 being unaffected 97. Finally, polarization splitter 78 acts on signal 97 to produce output signals 98. Again, in this situation no quadrature signal is provided on the upper output ports with the output power being distributed equally on both channels. However, in the lower channels, the polarization state 97 results in an output '1' in the lower channel which is interpreted as an output equivalent to binary (0).

Where quadrature signal decoding is required, the top two channel outputs provide an indicator of the phase response of the signals.

Figure 14:
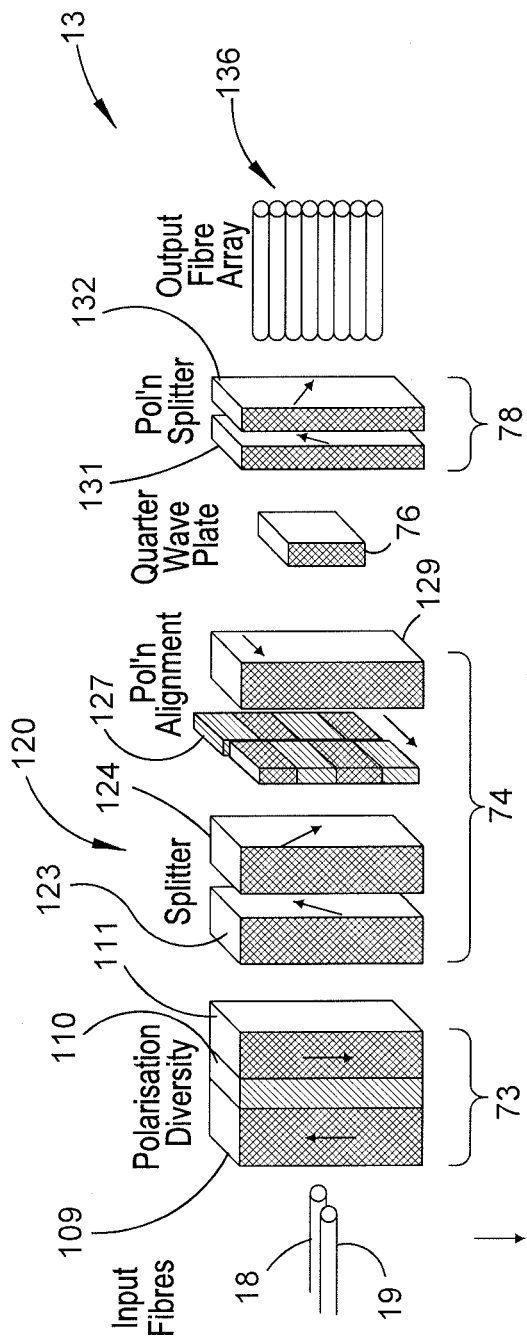
FIG. 14 illustrates a further form of implementation of the arrangement of FIG. 9.
Figure 15:
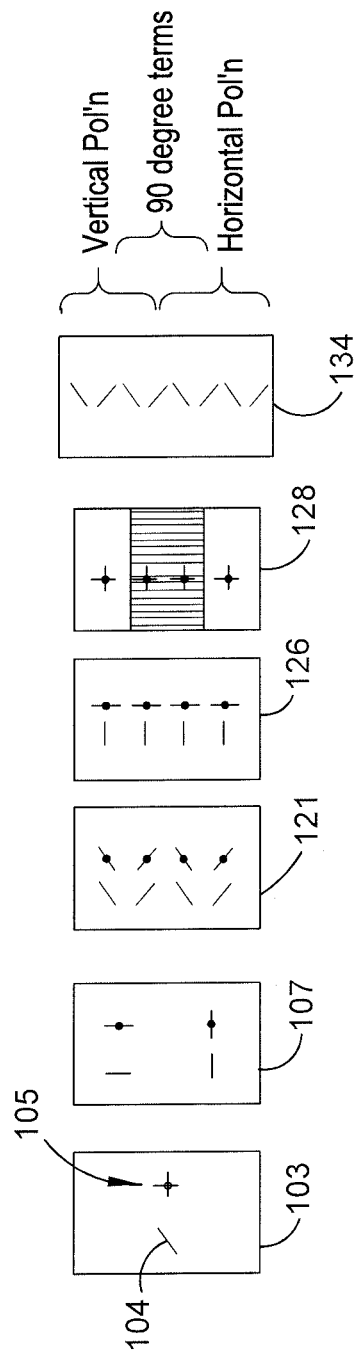
FIG. 15 illustrates the polarization transitions for light travelling through the arrangement of FIG. 14.

FIG. 14 illustrates one form of implementation of the CPA in more detail. FIG. 14 needs to be ideally read in conjunction with FIG. 15 which illustrates a corresponding evolution of polarization states for the arrangement of FIG. 14. The probe signal and reference oscillator signal are input on input fibers 18, 19. Referring to the polarization states, the reference signal is input having an input polarization 104 of 45 degrees to the vertical. The received probe signal has a randomly oriented polarization state 105 depending on the state of the reflected state.

The polarization diversity element 73 acts to spatially separate orthogonal polarization components producing polarization outputs 107. The diversity element consists of a first walk off crystal 109, a half wave plate 110 and a second walk off crystal 111. As is known in the art, the walk off crystals 109, 111 act to spatially separate orthogonal polarization states. The walk off crystal can be a birefringent $YVO_4$ (Ytrium Vanadate) crystal with the optical axis aligned at approximately 45 degrees to the face of the crystal in the direction of the required separation of the polarization states. In this case, the first walk off crystal 109 acts to translate the horizontally polarized input in a vertical manner. The half wave plate 110 rotates both polarization states by $\pi/2$ degrees. The second walk off crystal 111 thereafter translates the newly horizontal polarization state downwards. The net result of this operation, as will be evident to those skilled in the art, is to separate the horizontal and vertical components of the input signals to produce polarization outputs 107.

Next, the polarization splitter element 120 acts to power split the spatially separated signals 107 into corresponding polarization outputs 121. The splitter consists of two walk off crystals 123, 124. The crystals are oriented at +45 degrees and −45 degrees to the horizontal axis respectfully. The resulting effect of the two walk off crystals is illustrated in polarization state diagram 121 which illustrates that each of the previous polarization states 107 have been rotated and divided into two components. The polarization state of each component being at +/−45 degrees to the horizontal.

Next, a half wave plate array 127 acts to align the polarization states into vertical and horizontal components 126. The walk off crystal 129 translates the vertical polarization component so that it overlaps with the horizontal components as indicated 128.

The quarter wave plate 75 is placed centrally to act on the middle two channels only and acts to delay one polarization component relative to the other by π/4 radians. This provides for determining the quadrature phase terms and allows an unambiguous determination of the relative phase between the probe signal and reference signal via analysis of the horizontal and vertical polarization states with a 90 degrees offset in the phase.

The polarization splitter 76 comprises walk off crystals 131, 132 aligned at +/−45 degrees to the horizontal respectively. The polarization splitter 76 acts to distribute the power of the polarization states 128 for output on output fiber array 136. The outputs include vertical polarization outputs, horizontal polarization outputs and 90 degree delay terms. The arrangement provides for a means for processing polarization and phase encoded information in an optical signal. Alternatively, the output can be to a series of photodetectors.

Figure 16:
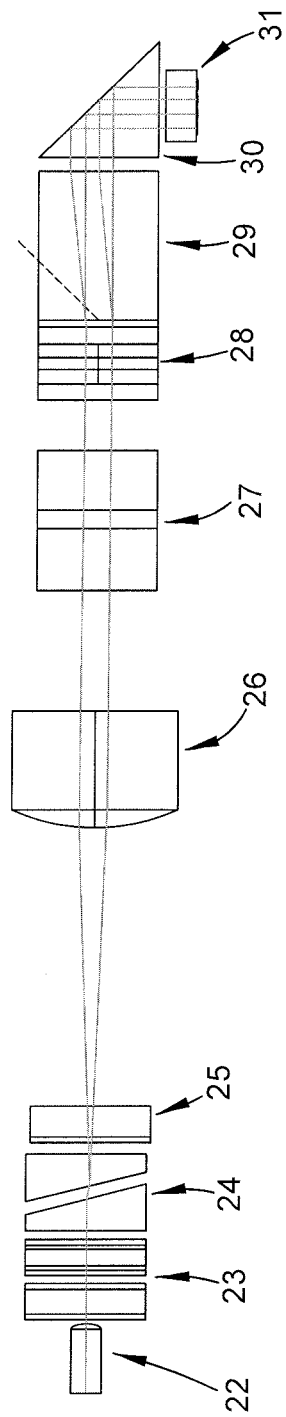
FIG. 16 illustrates a side plan view of one form of simulated optical train.
Figure 17:
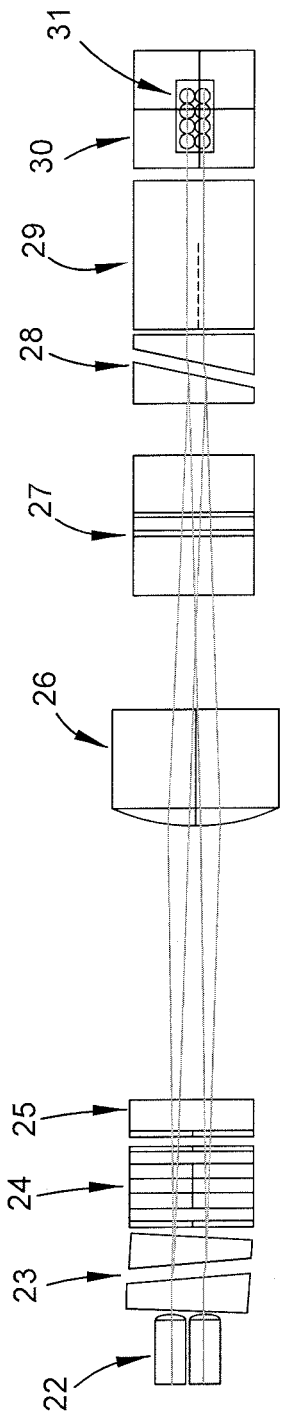
FIG. 17 illustrates a top plan view of the simulated optical train of FIG. 15.

FIG. 16 and FIG. 17 illustrates one form of simulated optical train implementing the arrangement of FIG. 14 with FIG. 16 illustrating a side plan view and FIG. 17 illustrating a corresponding top plan view. FIGS. 16 and 17 are ideally read in conjunction with FIG. 24 which illustrates a corresponding evolution of polarization states and waveplate locations for the arrangement of FIGS. 16 and 17.

Figure 24:
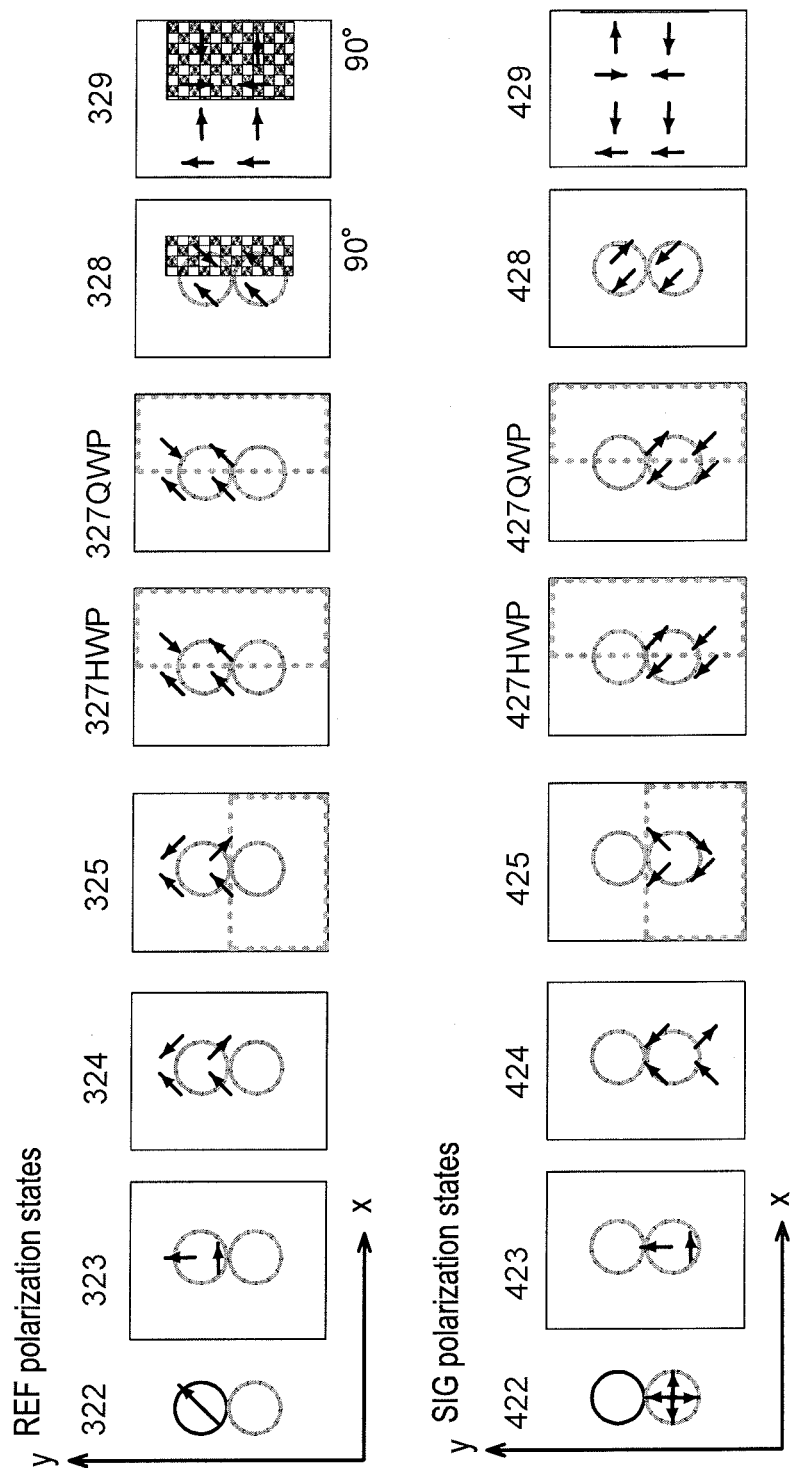
FIG. 24 tracks the polarization states through the implementation of the Coherent Polarization Analyzer (CPA) described in FIGS. 16 and 17.

In this implementation, the polarization separation is achieved by wedges rather than walk off crystals. The components are described by FIGS. 16-17 while the polarization states through the device are shown in FIG. 24. The top series of polarization states shows the evolution of polarization states (322 to 329) within the reference signal. The bottom series of polarization states (422 to 429) illustrates the transitions of the return input signal state. Initially, a 1×2 input lens array 22 couples light from the fiber into the CPA with light from the reference signal having a predetermined polarization state 322 and light from the return input signal assumed to be made up of arbitrary polarization state 422. Following the lens two birefringent wedge pairs (23 and 24) separate the light into orthogonal polarization states creating 8 beams 324, 424 as shown in FIG. 24. A half waveplate array element 25 with fast axis oriented in the y axis (all polarization states are taken with reference to the axis provided in FIG. 24) applies a polarization rotation to the bottom selected signal beams resulting in the polarization states 425. The upper polarization states 325 are unaffected. The beams are then focused by a lens 26 into a half wave plate/quarter waveplate array 27, which applies another polarization rotation to selected beams as seen in FIG. 24, to produce polarization states 327HWP, 427HWP. The half waveplate 27 is oriented such that the fast axis is oriented in the x axis, with the optical axis oriented into the plane. The quarter waveplate 27 applies a 90° phase shift to select pulses to produce polarization states 327QWP and 427QWP respectively. In the above implementation the fast axis is oriented at −45°. The light then passes through another birefringent wedge 28 to combine the beams 328, 428, following which the light passes through a beam displacer 29 to produce output polarization states 329, 429. The light is then incident on a turning prism 30 and reflected by a mirror onto a 2×4 output lens array. Combining the corresponding local oscillator and signal pulses gives output signals 329, 429 being $E_{SIG}+E_{LO}$, $E_{SIG}-E_{LO}$, $E_{SIG}+jE_{LO}$ and $E_{SIG}-jE_{LO}$ for each polarization state, as required c.f. FIG. 8. The light can then be coupled into fibers or directly onto a photodiode array.

In review, the polarization diversity and splitting in addition to the polarization alignment portions are provided by optical components 23-25 and 27-29 which include a series of polarization wedges and wave plates that act only on predetermined portions of the signals. The lens 26 is also provided for focusing the input beams. The quarter wave plate 27 acts only on predetermined portions of the signal train. The output signals are then reflected onto lens array 31 by prism 30. The lens array can focuses the light either into a fiber array or directly onto the photodetectors.

EXAMPLE IMPLEMENTATIONS

Figure 6:
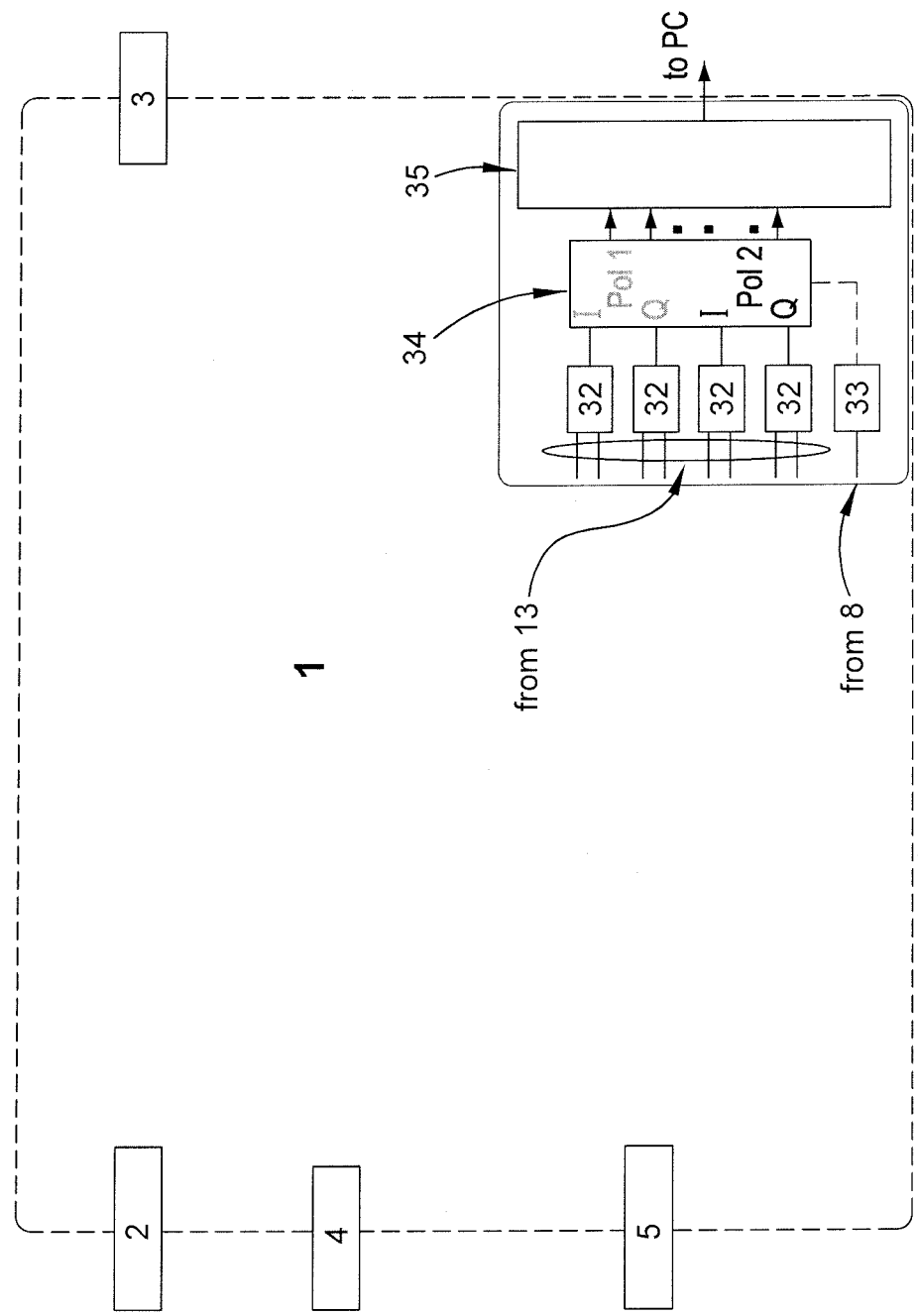
FIG. 6 is a schematic block diagram of the electrical sampling components of an embodiment.
Figure 7:
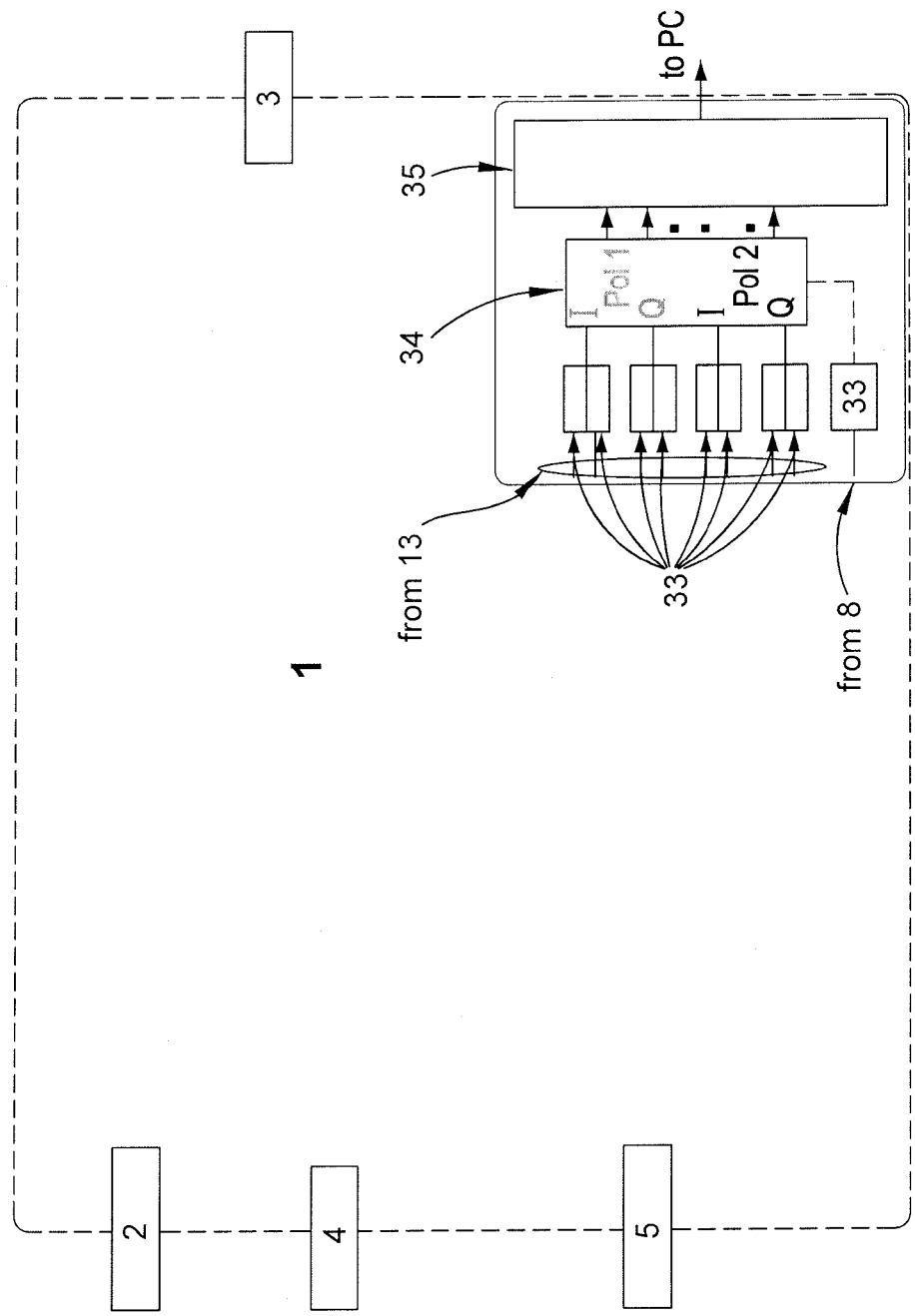
FIG. 7 is a schematic block diagram of the electrical sampling components of an embodiment.

The integration of the CPA into an OCT system can be seen initially in FIG. 6 and FIG. 7. FIG. 6 and FIG. 7 show example electronic connections.

Turning initially to FIG. 6, the eight optical output ports of the CPA 13 of the optical engine 1 are connected to four balanced photo-detectors 32, each balanced photo-detector corresponding to a quadrature in each polarization. The use of balanced photo-detectors can eliminate the need for the removal of the DC bias component of the inteferometric signal later on in the processing.

FIG. 7 illustrates an alternative arrangement showing the use of standard photo-detectors 33 in the system. In this configuration the DC bias is removed later on in the signal processing.

In either case, the signal is then passed through a data acquisition card (DAQ) 34 which converts the analogue signal into a digital signal and samples it. A further photodetector 33 connected between the trigger path 8 and the DAQ 34 is used to provide a trigger to provide linear triggering. The use of the internal triggering circuit (10, 8 and 34) is the preferred form for a SS-OCT configuration. The internal trigger on the DAQ may be used to simplify the device, but comes at the cost of increased computational complexity as this requires a resampling of the acquired data to linearize it in the wave space. An external trigger can also be used.

Once the data has been sampled it is then passed to a field programmable gate array (FPGA) or application specific integrated circuit (ASIC), or other electronics capable of DSP, denoted by 35. In 35 the signal processing is done, including buffering, Fourier transform, scaling, summing and calibration needed on the signal, along with some simple digital signal processing (DSP). The data is then transferred to a PC for further data processing. The FPGA (or ASIC) 35 may be removed and the data then forwarded directly to a DSP, Microcontroller or Microprocessor. This simplification may come at the cost of an increased image processing time.

Example

Homodyne SS-OCT System Integration

Figure 18:
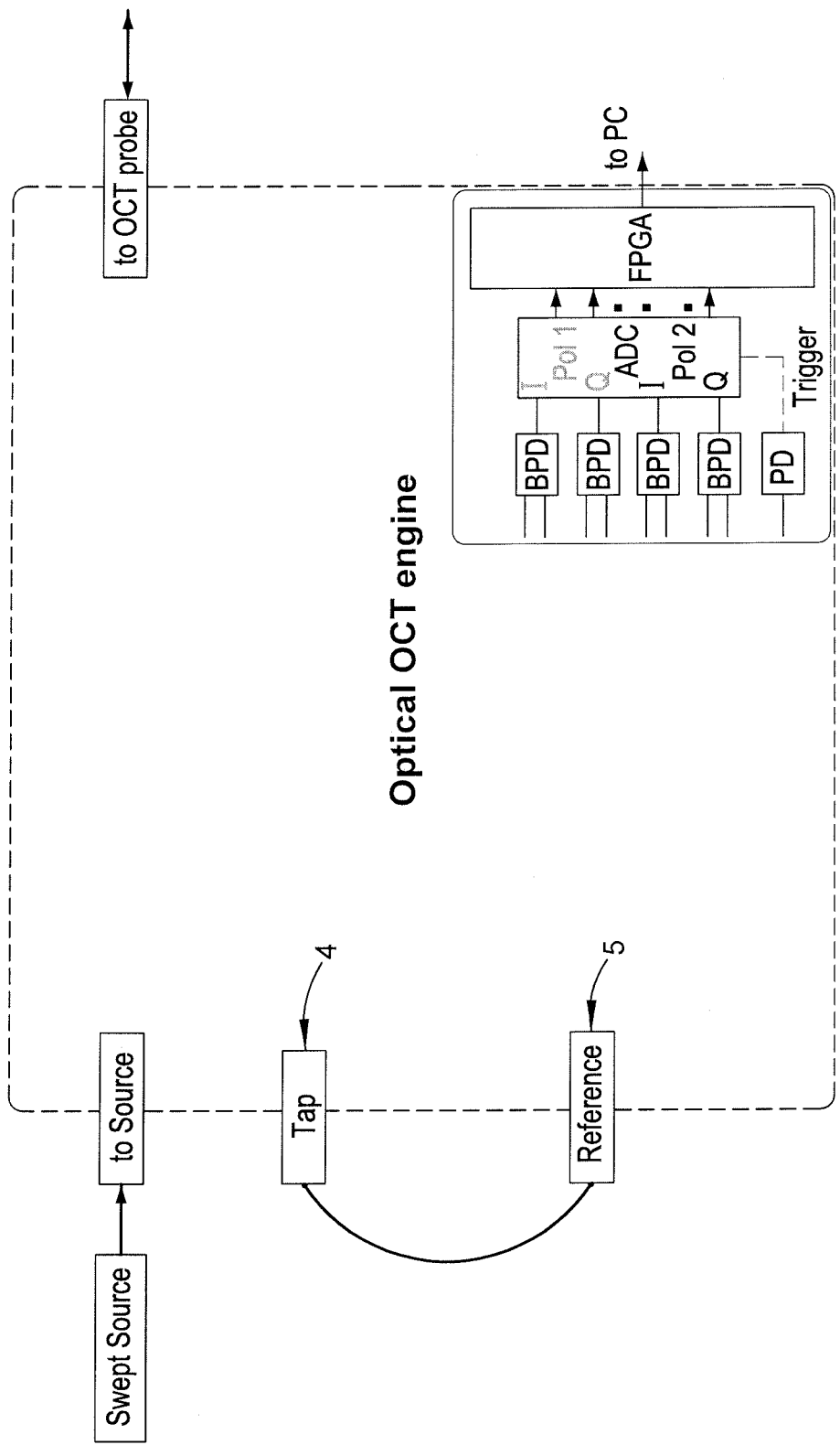
FIG. 18 is an example block diagram illustrating the present invention configured for use in a swept source optical coherence tomography system with homodyne detection

FIG. 18 illustrates the integration of the CPA into a swept source homodyne system. The integration is accomplished by the completion of an optical light path between 4 and 5 of suitable length. Exact matching of the path lengths 6 and 7 (In FIG. 5) can be accomplished using the tunable delay line 15.

The following mathematical framework should ideally be considered with reference to FIG. 8.

For an SS-OCT system it is possible to approximate the back-scattered wave from a sample E, in terms of a number of discrete reflectors, i.e.

$$E_{s,obj}(k, t) = \sum_n r_n A_i e^{i(kz_n - \omega_R t)}$$

where $r_n$ is the complex scalar reflectance of the $n^{th}$ sample reflector in the backwards direction, and $z_n$ is the position of the nth sample reflector and $A_i$ is an incident wave amplitude. The reference signal can be written as:

$$E_{LO}(k,t) = A_{LO} e^{i(kz_{LO} - \omega_{LO} t)}$$

where $A_{LO}$ is the amplitude of the (i.e. amplitude), and $z_{LO}$ is the corresponding distance. As homodyne detection is being used, $\omega_{LO} = \omega_R$ and, considering only one polarization state, the photocurrents at 36 and 37 of FIG. 8 can be written as:

$$i_{PD1,k}(t) = |E_{s,obj} + E_{LO}|^2 =$$

$$|g(t)|\left\{|A_{LO}|^2 + \left|\sum_n A_i r_n\right|^2 + 2\Re e\left\{A_{LO}^* A_i \sum_n r_n e^{i(k(z_n - z_R))}\right\} + 2\Re e\left\{\sum_n \sum_{m \neq n} r_n r_m^* e^{i(k(z_n - z_m))}\right\}\right\}$$

$$i_{PD2,k}(t) = |E_{s,obj} - E_{LO}|^2 = |g(t)|\left\{|A_{LO}|^2 + \left|\sum_n A_i r_n\right|^2 - 2\Re e\left\{A_{LO}^* A_i \sum_n r_n e^{i(k(z_n - z_R))}\right\} + 2\Re e\left\{\sum_n \sum_{m \neq n} r_n r_m^* e^{i(k(z_n - z_m))}\right\}\right\}$$

where the first two terms are non-interferometric artifacts, the third term is a cross correlation interferometric term and the fourth term is a autocorrelation artifact and g(t) is the temporal coherence function. Assuming the use of balanced photo-detectors results in:

$$i_{BPD1,k}(t) = 2|g(t)|\Re e\left\{A_{LO}^* A_i \sum_n r_n e^{i(k(z_n - z_R))}\right\}$$

Likewise, for the other pair of photo-detectors 38 and 39, the following equations result:

$$i_{PD3,k}(t) = |E_{s,obj} + jE_{LO}|^2 =$$

$$|g(t)|\left\{|A_{LO}|^2 + \left|\sum_n A_i r_n\right|^2 + 2\Im m\left\{A_{LO}^* A_i \sum_n r_n e^{i(k(z_n - z_R))}\right\} + 2\Re e\left\{\sum_n \sum_{m \neq n} r_n r_m^* e^{i(k(z_n - z_m))}\right\}\right\}$$

$$i_{PD4,k}(t) = |E_{s,obj} - jE_{LO}|^2 = |g(t)|\left\{|A_{LO}|^2 + \left|\sum_n A_i r_n\right|^2 - $$

$$2\Im m\left\{A_{LO}^* A_i \sum_n r_n e^{i(k(z_n - z_R))}\right\} + 2\Re e\left\{\sum_n \sum_{m \neq n} r_n r_m^* e^{i(k(z_n - z_m))}\right\}\right\}$$

giving with balanced photodetection $$i_{BPD2,k}(t) = 2|g(t)|\Im m\left\{A_{LO}^* A_i \sum_n r_n e^{i(k(z_n + z_R))}\right\}$$

Noting that for SS-OCT, the wave number k is a function of time, it is possible to parameterize k by t to get $$k(t) = k_0 + t\frac{dk}{dt}$$

where $$\frac{dk}{dt}$$

is the sweep velocity. Hence letting $$\omega_n = \frac{dk}{dt}(z_n - z_R) \text{ and } \phi_n = k_0(z_n - z_R)$$

we find $$i_{BPD1}(t) = 2|g(t)|\Re e\left\{A_{LO}^* A_i \sum_n r_n e^{i(\phi_n + \omega_n t)}\right\}$$

$$i_{BPD2}(t) = 2|g(t)|\Im m\left\{A_{LO}^* A_i \sum_n r_n e^{i(\phi_n + \omega_n t)}\right\}$$

This shows the complete phase and amplitude information in the sweep is obtained. As the above photocurrents are dependent on only on time varying frequency, we can use wave-number triggering. As the complex function is completely determined, the complex conjugate artifact is removed and phase information is recovered. Similarly, like expressions can be found for the other polarization state, giving the output for 20 and 21 as $$(i_{BPD1,x}) + j(i_{BPD1,y}) = 2|g(t)|A_R A_{S,x}\left[\sum_n r_n e^{i(\phi_n + \omega_n t)}\right]$$

$$(i_{BPD1,y}) + j(i_{BPD2,y}) = 2|g(t)|A_R A_{S,y}\left[\sum_m r_m e^{i(\phi_m + \omega_m t)}\right]$$

The use of a polarization diverse configuration offers many benefits. Polarization fading can be easily compensated for. Birefringence of the sample can be measured. Large amounts of polarization maintaining fiber, using in other designs, can be eliminated though polarization tracking algorithms or calibration.

Figure 19:
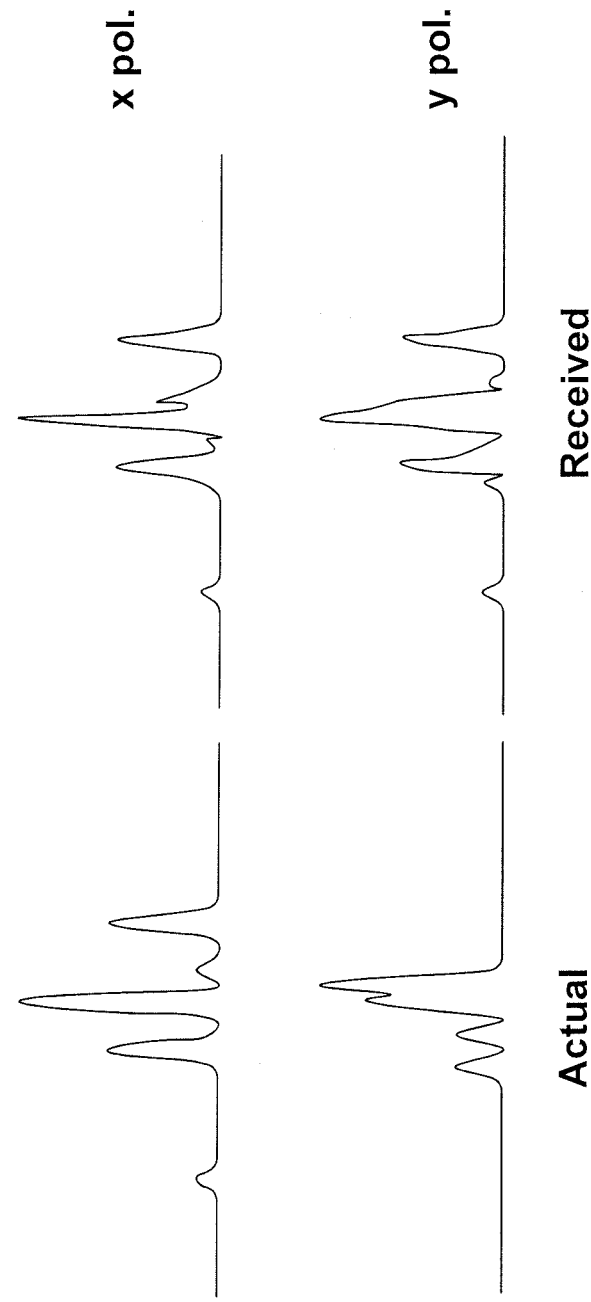
FIG. 19 is a plot showing the effect of polarization rotation on the received optical coherence tomography A-scan compared to the actual results for a set of polarization dependent discrete reflectors.

An example of polarization rotation compensation is described below. In general, these unwanted effects, such as birefringence in the fibers, can be modeled as an unwanted polarization rotation. Mathematically this situation corresponds to the received photocurrents being $$i_{BPD1,x} = 2|g(t)|\Re e\left\{\alpha A_R^* A_x \sum_n r_n e^{i(\phi_n+\omega_n t)} + \beta A_{LO}^* A_y \sum_m r_m e^{i(\phi_m+\omega_m t)}\right\}$$

$$i_{BPD2,x} = 2|g(t)|\Im m\left\{\alpha A_R^* A_x \sum_n r_n e^{i(\phi_n+\omega_n t)} + \beta A_{LO}^* A_y \sum_m r_m e^{i(\phi_m+\omega_m t)}\right\}$$

$$i_{BPD1,y} =$$
$$2|g(t)|\Re e\left\{-\beta^* A_R^* A_x \sum_n r_n e^{i(\phi_n+\omega_n t)} + \alpha^* A_{LO}^* A_y \sum_m r_m e^{i(\phi_m+\omega_m t)}\right\}$$

$$i_{BPD2,y} = 2|g(t)|\Im m\left\{-\beta^* A_R^* A_x \sum_n r_n e^{i(\phi_n+\omega_n t)} + \alpha^* A_{LO}^* A_y \sum_m r_m e^{i(\phi_m+\omega_m t)}\right\}$$

where $\alpha$ and $\beta$ correspond to the polarization vector rotation, and $r_m$ and $r_n$ correspond to the reflectivity in the different polarization states. Simplifying the above we can write the complete received photocurrents 20 and 21 as $$(i_{BPD1,x}) + j(i_{BPD1,y}) = 2|g(t)|A_R A_S\left[\alpha\sum_n r_n e^{i(\phi_n+\omega_n t)} + \beta\sum_m r_m e^{i(\phi_m+\omega_m t)}\right]$$

$$(i_{BPD1,y}) + j(i_{BPD2,y}) =$$
$$2|g(t)|A_R A_S\left[-\beta^*\sum_n r_n e^{i(\phi_n+\omega_n t)} + \alpha^*\sum_m r_m e^{i(\phi_m+\omega_m t)}\right]$$

respectively. Taking the Fourier transform to resolve the reflector depth profile as in SS-OCT we obtain $$FT\{(i_{BPD1,x}) + j(i_{BPD1,y})\} =$$
$$2|g(\omega)| * A_R A_S\left[\alpha\sum_n r_n \delta(\omega-\omega_n)e^{i(\phi_n)} + \beta\sum_m r_m \delta(\omega-\omega_m)e^{i(\phi_m)}\right]$$

$$FT\{(i_{BPD1,y}) + j(i_{BPD2,y})\} =$$
$$2|g(\omega)| * A_R A_S\left[-\beta^*\sum_n r_n \delta(\omega-\omega_n)e^{i(\phi_n)} + \alpha^*\sum_m r_m \delta(\omega-\omega_m)e^{i(\phi_m)}\right]$$

where $$\omega_n = \frac{dk}{dt}(z_n - z_R)$$

and $\phi_n = k_0(z_n - z_R)$. This has the effect of mixing the signals as shown in FIG. 19.

Various methods to compensate for this rotation effect exist in the literature, primarily through making use of polarization switching (increasing the sweep time) or a pre-calibration with a reference reflector. While both these methods are applicable to the above system, a software compensation algorithm is also proposed based on a modified probe design to provide real time polarization compensation at the cost of a slightly reduce imaging depth.

Figure 20:
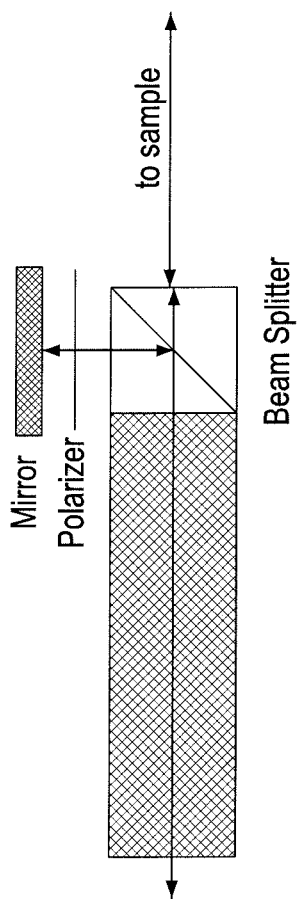
FIG. 20 illustrates one form of polarization control of the reference beam.
Figure 21:
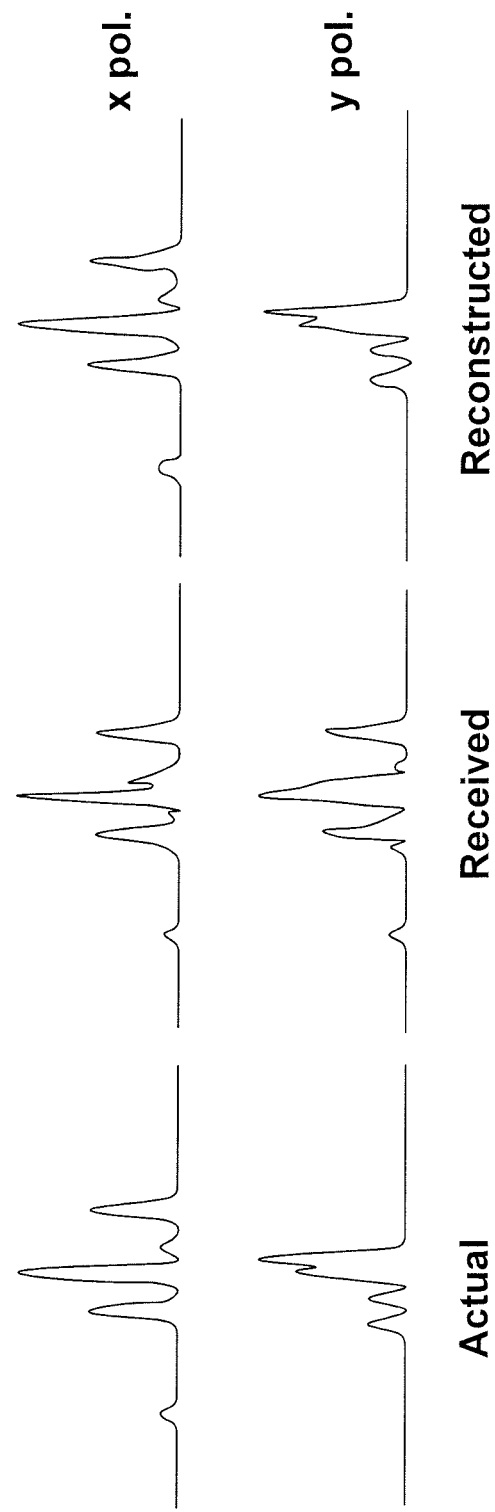
FIG. 21 is a plot showing the effect of polarization compensation on the received optical coherence tomography A-scan compared to the actual results for a set of polarization dependent discrete reflectors.

The modified probe consists of a polarization dependent reference reflector introduced in the probe at a position corresponding to a known reference depth. An example of this design is shown in FIG. 20. In one design there is paced an effective reflectance at an extremity of the imaging range to allow for the largest imaging depth possible. Mathematically, in the A scan this corresponds to the reflectance profiles at the depth $z_{ref}$ of $$FT\{E_X\}(\omega, z_{ref}) = 2|g(\omega, z_{ref})| * A_{LO} A_S[(\alpha)r_z \delta(\omega-\omega_z)e^{i(\phi_z)}]$$

$$FT\{E_Y\}(\omega, z_{ref}) = 2|g(\omega, z_{ref})| * A_{LO} A_S[(-\beta^*)r_z \delta(\omega-\omega_z)e^{i(\phi_z)}]$$

Given the relation $\alpha^2 + \beta^2 = 1$, the values of $\alpha$ and $\beta$ that unwind the rotation (and hence allow for the calculation of $\alpha$ and $\beta$) can be found by minimizing one value of the reflectivity point corresponding to $z_{ref}$ whilst maximizing the other. This can be accomplished using various techniques, ranging from a brute force search to more efficient minimization algorithms found in literature. Due to the linearity of the Fourier transform, the polarization rotation can be unwound by a simple multiplication once the values of $\alpha$ and $\beta$ are found. The addition of a further reference reflection at a different depth $z_{ref2}$ for the orthogonal polarization allows for complete compensation at the cost of further reduced depth.

Example

Heterodyne SS-OCT System Integration

Figure 22:
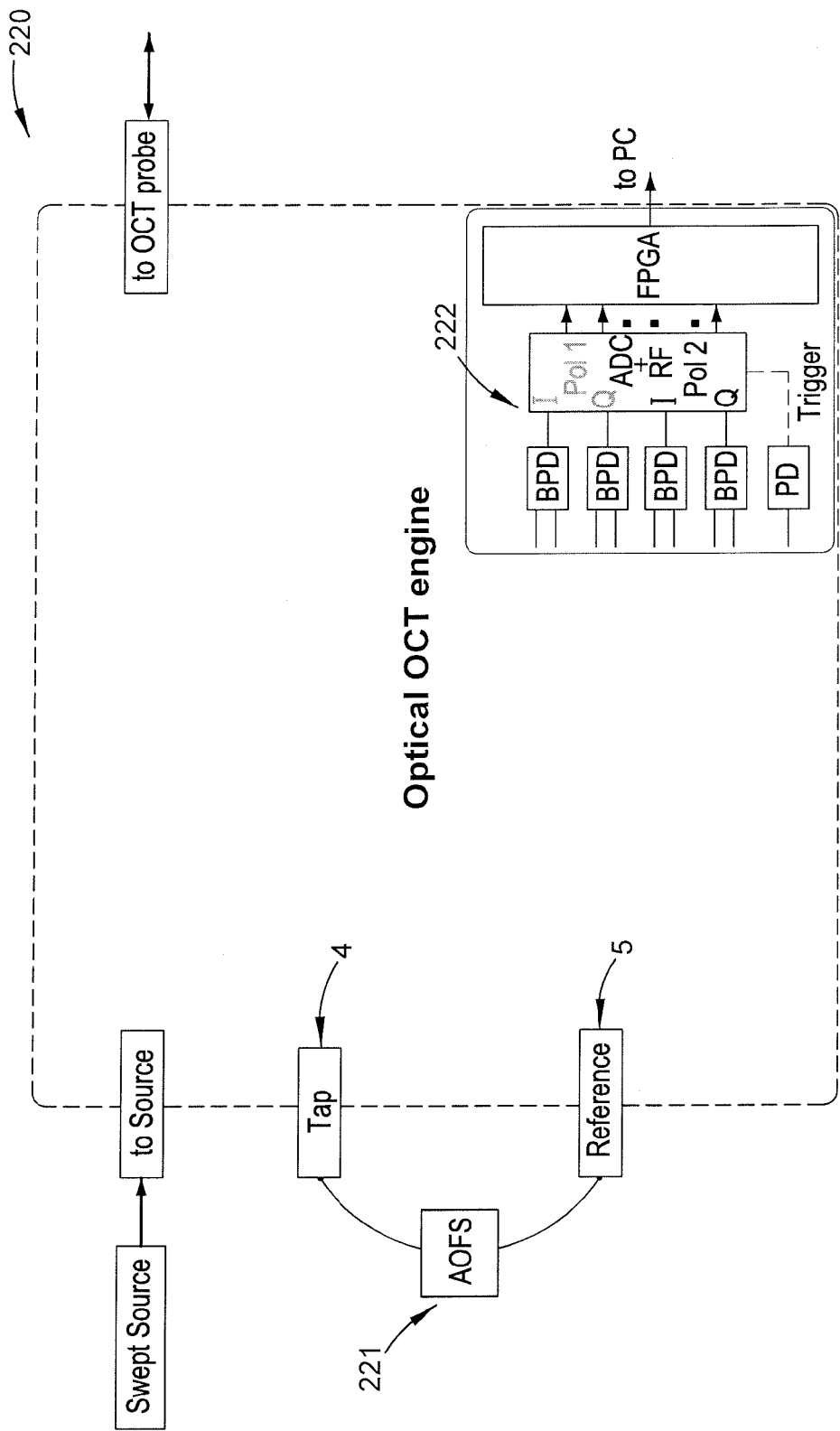
FIG. 22 is an example block diagram illustrating the present invention configured for use in a swept source optical coherence tomography system with heterodyne detection.

A heterodyne swept source OCT architecture 220 is shown in FIG. 22. In this embodiment, an acousto-optical frequency shifter (AOFS) 221 is integrated into the optical path between 4 and 5 to provide a frequency shift between the sample arm 7 and reference arm 6. Radio frequency electronics 222 are utilized between the photo-detectors and the DAQ to convert the signal to an appropriate IF frequency for sampling and processing. In both the heterodyne and homodyne SS-OCT systems, the arrangement can be triggered using an internal triggering line.

Example

TD-OCT System Integration

Figure 23:
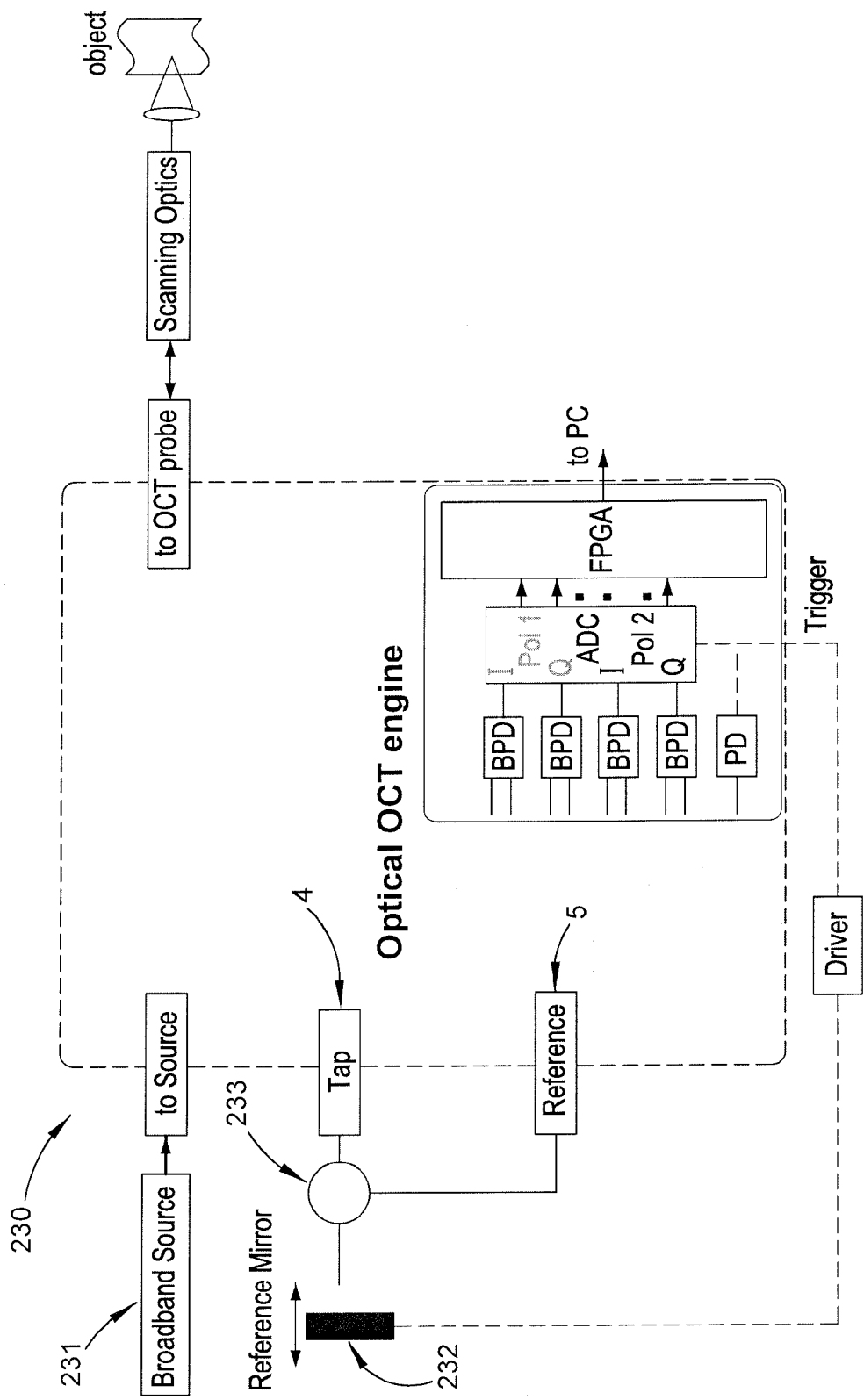
FIG. 23 is an example block diagram illustrating the present invention configured for use in a time domain optical coherence tomography system.

A time domain OCT implementation 230 is shown in FIG. 23. The source input 231 consists of broadband source with low coherence length. The reference arm path consists of a tunable reference mirror 232 and circulator 233. The reference signal passes through the circulator 233 and onto the reference mirror 232. As in TD-OCT systems, the position of this mirror is variable and determined by a signal from an electrical driver 234. The reference mirror reflects the signal back through the circulator 233, which passes the reference signal through to the input port 5 and onto the CPA 13. For this configuration, triggering of the DAQ can be from the drive signal supplied to the mirror and not the internal triggering circuit.

Example

No Quadrature Signal Implementation

The OCT systems described so far can be further simplified at the expense of reduced functionality. By ignoring the quadrature component of the signal, the receiver electronics are reduced and the resulting signal processing simplified. When the quadrature component is ignored, minor modifications to the CPA 13 remove a 3 dB signal loss, due to a further polarization splitting, but still provide the advantages associated with polarization mixing. One such modification to remove the quadrature signal is realized by removing the quarter waveplate 75 and power splitter 120 seen in FIG. 14.

The foregoing describes preferred forms of the present invention. Modifications, obvious to those skilled in the art can be made thereto without departing from the spirit and scope of the present invention.

We claim:

1. A method of analysis of a sample, including the steps of:
   (a) splitting an input optical beam into a probe beam and reference beam;
   (b) utilizing the probe beam to interrogate a sample and obtaining a return sample beam therefrom;
   (c) manipulating the reference beam into a predetermined polarization state;
   (d) polarization mixing the return sample beam and reference beam producing a series of polarization mixed beams; and
   (e) analyzing the polarization components of the series of mixed beams.

2. A method as claimed in claim 1 wherein said mixing step further includes the steps of:
   dividing the reference beam into substantially polarization orthogonal reference components;
   dividing the return sample beam into substantially polarization orthogonal return sample components; and
   mixing the reference components with the sample components to produce a series of mixed beams.

3. A method as claimed in claim 2 wherein said mixing includes obtaining sum and difference components of the mixed reference components.

4. A method as claimed in claim 2 wherein said substantially polarization orthogonal reference components comprise horizontal and vertical components.

5. A method as claimed in claim 1 wherein said analyzing step includes outputting the quadrature signal components of the combination of the probe and reference beam.

6. A method as claimed in claim 1 wherein said splitting step further comprises splitting the input optical beam into a triggering beam and said analyzing step further comprises utilizing the triggering beam to initiate sampling of the polarization components.

7. A method as claimed in claim 1 further including monitoring one or more characteristics of said input optical beam and selectively modifying said polarization mixed beams in response to said monitoring.

8. An optical signal analysis system comprising:
   an optical source for projecting an input optical beam;
   a beam splitter interconnected to the optical source for splitting the input optical beam into a probe beam and reference beam;
   a sampling unit for utilizing the probe beam to interrogate a sample and obtain a return probe beam therefrom;
   a length matching unit for correlating the reference beam path length with the return probe beam path length;
   a polarization manipulation unit for manipulating the polarization state of the correlated reference beam into a predetermined polarization state; and
   a polarization analysis unit for polarization mixing substantially orthogonal polarization components of the correlated reference beam with the return probe beam.

9. A system as claimed in claim 8 wherein said polarization manipulation unit and said polarization analysis unit are integrated within a coherent optical receiver unit.

10. A system as claimed in claim 8 wherein said polarization analysis unit is configured to:
    divide the reference beam into substantially polarization orthogonal reference components;
    divide the return probe beam into substantially polarization orthogonal return probe components; and
    mix the reference components with the probe components to produce a series of mixed beams.

11. A system as claimed in claim 10 wherein the polarization analysis unit obtains sum and difference components of the mixed reference components.

12. A system as claimed in claim 8 wherein said polarization analysis unit outputs the quadrature signal components of the combination of the probe and reference beam.

13. A system as claimed in claim 8 further including a second beam splitter for splitting the input optical beam into a triggering beam and said polarization analysis unit utilizes the triggering beam to initiate sampling of the polarization components.

14. A system as claimed in claim 8 wherein said probe and reference beams are propagated along optical paths that are free of waveguides.

15. A receiver for an Optical Coherence Tomography (OCT) system, said receiver comprising:
    a first input port for receiving an OCT probe beam reflected from a sample;
    a second input port for receiving an OCT reference beam transmitted along an optical path substantially matched to the probe beam optical path;
    a polarization manipulation unit for:
       dividing said reference beam into substantially polarization orthogonal reference components; and
       dividing said probe beam into substantially polarization orthogonal probe components; and
    an analysis unit for polarization mixing reference and probe components to produce a series of mixed output beams.

16. A receiver as claimed in claim 15 wherein said analysis unit is a fiber coupled coherent receiver.

17. A receiver as claimed in claim 15 wherein said analysis unit includes:
    a first mixer for mixing a first orthogonal reference component with a first orthogonal probe polarization component to provide a first mixed signal;
    a second mixer for mixing a second orthogonal reference component with a second orthogonal probe polarization component to provide a second mixed signal; and
    an analyser for analysing said first and second mixed signals to determine the polarization or phase information in the Optical Coherence Tomography (OCT) probe beam.

18. A receiver as claimed in claim 17 wherein said analyser includes:
    a splitter for splitting the power of the first mixed signal into at least a first and second mixed sub-signals;
    a delay element for delaying one orthogonal polarization component of the first sub-signal relative to the second component by pi/2 radians to produce a phase delayed first sub-signal; and
    a dividing unit for dividing the phase delayed first sub signal into orthogonal components and the second mixed sub-signal into orthogonal components.

19. A receiver as claimed in claim 15 wherein said mixed output beams include the following four quadrature phase mixed beams in a first x polarization state:

$$E_x^z + E_x^R, E_x^z - E_x^R, E_x^z + iE_x^R, E_x^z + iE_x^R;$$

and the following four quadrature phase mixed beams in a second in a second y polarization state:

$$E_y^s + E_y^R, E_y^s - E_y^R, E_y^s + iE_y^R, E_y^s + iE_y^R;$$

where E represents an electric field strength, R indicates a reference signal component and S indicates a probe signal component.

20. A receiver as claimed in claim 19 including four balanced photodetectors, each configured for simultaneously receiving a corresponding quadrature phase beam of each polarization state.

* * * * *